United States Patent [19]
Epstein et al.

[11] Patent Number: 5,599,681
[45] Date of Patent: Feb. 4, 1997

[54] ACTIVATION-STATE-SPECIFIC PHOSPHOPROTEIN IMMUNODETECTION

[75] Inventors: Richard J. Epstein, Brookline; Charles D. Stiles, Newton, both of Mass.

[73] Assignee: Dana-Farber Cancer Institute, Inc., Boston, Mass.

[21] Appl. No.: 324,421

[22] Filed: Oct. 13, 1994

Related U.S. Application Data

[63] Continuation of Ser. No. 918,370, Jul. 23, 1992, abandoned, which is a continuation-in-part of Ser. No. 866,728, Apr. 10, 1992, abandoned.

[51] Int. Cl.$^6$ .......................... G01N 33/53; G01N 33/574
[52] U.S. Cl. .......................... 435/7.23; 435/7.4; 436/547; 436/548; 436/543; 530/387.7; 530/387.9; 530/388.8; 530/388.85; 530/389.7
[58] Field of Search .................................. 435/7.23, 7.4; 436/547, 543, 548; 530/387.7, 387.9, 388.8, 388.85, 389.7

[56] References Cited

PUBLICATIONS

Lerner, R. A., "Tapping the immunological repertoire to produce antibodies of predetermined specificity,", Nature, vol. 299, pp. 592–596, 1982.

Campos-González et al, "Immunodefection of the Ligand-Activated Receptor for Epidermal Growth Factor", Growth Factors, vol. 4, pp. 305–316 (1991).

Epstein, RJ, et al., "Modulation of a $M_r$ 175,000 c-neu Receptor Isoform in G8/DHFR Cells by Serum Starvation", J. Biol. Chem., vol. 265, No. 18, pp. 10746–10751, Jun. 1990.

Kazlauskas, A., et al., "Autophosphorylation of the PDGF Receptor in the Kinase Insert Region Regulates Interactions with Cell Proteins", Cell, vol. 58, pp. 1121–1133, Sep. 1989.

Sausville, E. A., et al., "Tyrosine Kinases as a Target for Chemotherapy", Ann Oncol, vol. 3(suppl. 1), p. 62, 1992.

R. R. Roussel et al., "Selective binding of activated pp60$^{c-src}$ by an immobilized synthetic phosphopeptide modeled on the carboxyl terminus of pp60$^{c-src}$", Proc. Natl. Acad. Sci., vol. 88, Dec., 1991.

A. C. Nairn et al., "Serum antibodies that distinguish between the phospho-and dephospho-forms of a phosphoprotein", Nature, vol. 299, Oct. 21, 1982, pp. 734–736.

A. J. Czernik et al., "Production of Phosphorylation State-Specific Antibodies", Methods on Enzymology, vol. 201, 1991, pp. 264–283.

Yarden et al., "Agonistic antibodies stimulate the kinase encoded by the neu protooncogene in living cells but the oncogenic mutant is constitutively active" Proc. Nat'l Acad. of Sciences of the USA 87(7)2569–2573 (1990).

Kaplan et al., "Mechanisms of transformation by polyoma virus middle T antigen," Biochimica et Biophysica Acta 948:345–364 (1988).

Schaffhausen et al., "Antibody to the Nonapeptide Glu–Glu–Glu–Glu–Tyr–Met–Pro–Met–Glu Is Specific for Polyoma Middle T Antigen and Inhibits In Vitro Kinase Activity," J. Biol. Chem. 257(21):12467–12470 (1982).

Towbin et al., "Electrophoretic transfer of proteins from polyacrylamide gels to nitrocellulose sheets: Procedure and some applications," PNAS 76:4350–4354 (1979) (copy enclosed herewith).

Morrison et al., "Direct Activation of the Serine/Threonine Kinase Activity of Raf-1 through Tyrosine Phosphorylation by the PDGF β–Receptor," Cell 58:649–657 (1989) (copy enclosed herewith).

Tandon et al., "HER–2/neu Oncogene Protein and Prognosis in Breast Cancer," J. Clin. Oncol. 7:1120–1128 (1989) (this and all articles following submitted Jun. 10, 1992, S.N. 07/866,728).

Bishop, "The Molecular Genetics of Cancer," Science 235:305–311 (1987).

Klein et al., "Evolution of tumours and the impact of molecular oncology," Nature 315:190–195 (1985).

Varmus, "The Molecular Genetics of Cellular Oncogenes," Ann. Rev. Genet. 18:553–612 (1984).

Slamon et al., "Human Breast Cancer: Correlation of Relapse and Survival with Amplification of the HER–2/neu Oncogene," Science 235:177–182 (1987).

Varley et al., "Alterations to either c–erbB–2 (neu) or c–myc proto–oncogenes in breast carcinomas correlate with poor short–term prognosis," Oncogene 1:423–430 (1987).

Borg et al., "Her–2/neu Amplification Predicts Poor Survival in Node–positive Breast Cancer," Cancer Res. 50:4332–4337 (1990).

Paterson et al., "Correlation between c–erbB–2 Amplification and Risk of Recurrent Disease in Node–negative Breast Cancer," Cancer Res. 51:556–567 (1991).

Keating et al., "Ligand Activation Causes a Phosphorylation-dependent Change in Platelet–derived Growth Factor Receptor Conformation," J. Biol. Chem. 263:12805–12808 (1988).

Downing et al., "Peptide Antisera to Human Colony–Stimulating Factor 1 Receptor Detect Ligand–Induced Conformational Changes and a Binding Site for Phosphatidylinositol 3–Kinase," Mol. Cell. Biol. 11:2489–2495 (1991).

Hu et al., "Antibodies Specific for the Human Retinoblastoma Protein Identify a Family of Related Polypeptides," Mol. Cell. Biol. 11:5792–5799 (1991).

(List continued on next page.)

Primary Examiner—Toni R. Scheiner
Attorney, Agent, or Firm—Weingarten, Schurgin, Gagnebin & Hayes LLP

[57] ABSTRACT

Activation-state-specific and protein-specific antiphosphoprotein antibodies and methods for their production are disclosed. Also disclosed are methods for evaluating the prognosis and therapeutic outcome for patients using the antiphosphoprotein antibodies and methods for characterizing the activation state of a reversibly phosphorylated protein, kits including the antibodies for use in characterizing the activation state of a protein, and methods for evaluating the agonist or antagonist activity of pharmaceutically useful compounds towards the conversion of a specific protein from its inactive to its active state.

22 Claims, 10 Drawing Sheets

OTHER PUBLICATIONS

Gullick et al., "Antibodies to the autophosphorylation sites of the epidermal growth factor receptor protein–tyrosine kinase as probes of structure and function," EMBO J. 4:2869–2877 (1985).
Wang, "Isolation of Antibodies for Phosphotyrosine by Immunization with a v–abl Oncogene–Encoded Protein," Mol. Cell. Biol. 5:3640–3643 (1985).
Wildenhain et al., "p185$^{neu}$ is phosphorylated on tyrosine in human primary breast tumors which overexpress neu/erbB-2," Oncogene 5:879–883 (1990).
Epstein et al., "Extracellular Calcium Mimics the Actions of Platelet–derived Growth Factor on Mouse Fibroblasts," Cell Growth and Differentiation 3:157–164 (1992).
Akiyama et al., "The Transforming Potential of the c–erbB–2 Protein Is Regulated by Its Autophosphorylation at the Carboxyl–Terminal Domain," Mol. Cell. biol. 11:833–842 (1991).
Margolis et al., "All Autophosphorylation Sites of Epidermal Growth Factor (EGF) Receptor and HER2.neu Are Located in Their Carboxyl–terminal Tails," J. Biol. Chem. 264:10667–10671 (1989).
Bischoff et al., "Human p53 is phosphorylated by p60–cdc2 and cyclin B–cdc2," Proc. Natl. Acad. Sci. USA 87:4766–4770 (1990).
Hanks et al., "The Protein Kinase Family: Conserved Features and Deduced Phylogeny of the Catalytic Domains," Science 241:42–52 (1988).
Yarden et al., "Structure of the receptor for platelet–derived growth factor helps define a family of closely related growth factor receptors," Nature 323:226–232 (1986).
Hunter, "A Tail of Two src's: Mutatis Mutandis," Cell 49:1–4 (1987).
Cobb et al., "Regulation of the Oncogenic Activity of the Cellular src Protein Requires the Correct Spacing between the Kinase Domain and the C–Terminal Phosphorylated Tyrosine (Tyr–527)," Mol. Cell. Biol. 11:5832–5838 (1991).
Lees et al., "The retinoblastoma protein is phosphorylated on multiple sites by human cdc2," EMBO J. 10:4279–4290 (1991).
Denner et al., "Regulation of Progesterone Receptor–Mediated Transcription by Phosphorylation," Science 250:1740–1742 (1990).
Kemppainen et al., "Androgen Receptor Phosphorylation, Turnover, Nuclear Transport, and Transcriptional Activation," J. Biol. Chem. 267:968–974 (1992).
Hazan et al., "Identification of Autophosphorylation Sites of HER2/neu," Cell Growth and Differentiation 1:3–7 (1990).
Weiner et al., "A point mutation in the neu oncogene mimics ligand induction of receptor aggregation," Nature 339:230–231 (1989).
Williams, "Signal Transduction by the Platelet–Derived Growth Factor Receptor," Science 248:1564–1570 (1989).
Hermansson et al., "Endothelial cell hyperplasia in human glioblastoma: Coexpression of mRNA for platelet–derived growth factor (PGDF) B chain and PDGF receptor suggests autocrine growth stimulation," Proc. Natl. Acad. Sci. USA 85:7748–7752 (1988).
Fahrer et al., "Expression of c–sis and Other Cellular Proto–oncogenes in Human Sarcoma Cell Lines and Biopsies," Int. J. Cancer 44;652–657 (1989).
Heldin et al., "Aberrant expression of receptors for platelet–derived growth factor in an anaplastic thyroid carcinoma cell line," Proc. Natl. Acad. Sci. USA 85:9302–9306 (1988).
Cartwright et al., "Activation of the pp60$^{c-src}$ protein kinase is an early event in colonic carcinogenesis," Proc. Natl. Acad. Sci. USA 87558–562 (1990).
Kim et al., "PDGF Stimulation of Inositol Phospholipid Hydrolysis Requires PLC–yl Phosphorylation on Tyrosine Residues 783 and 1254," Cell 65:435–441 (1991).
Boulton et al., "ERKs: A Family of Protein–Serine/Threonine Kinases That Are Activated and Tyrosine Phosphorylated in Response to Insulin and NGF," Cell 65:663–675 (1991).
Malkin et al., "Germ Line p53 Mutations in a Familial Syndrome of Breast Cancer, Sarcomas, and Other Neoplasms," Science 250:1233–1238 (1990).
Gannon et al., "Activating mutations in p53 produce a common conformational effect. A monoclonal antibody specific for the mutant form," EMBO J. 9:1595–1602 (1990).
Thompson et al., "p53 Allele Losses, Mutations and Expression in Breast Cancer and Their Relationship to Clinico–Pathological Parameters," Int. J. Cancer 50:528–532 (1992).
Denner et al., "Hormonal Regulation and Identification of Chicken Progesterone Receptor Phosphorylation Sites," J. Biol Chem. 265:16548–16555 (1990).
Misrahi et al., "Complete Amino Acid Sequence of the Human Progesterone Receptor Deduced From Cloned cDNA," Biochem. Biophys. Res. Comm. 143:740–748 (1987).

GROWTH FACTOR RECEPTOR SUPERFAMILIES

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: C-terminal ( x i ) SEQUENCE DESCRIPTION: SEQ ID NO:1:

```
Ala  Glu  Asn  Pro  Glu  Tyr  Leu  Gly  Leu  Asp  Val  Pro  Val
1                   5                        10
```

( 2 ) INFORMATION FOR SEQ ID NO:2:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: C-terminal ( x i ) SEQUENCE DESCRIPTION: SEQ ID NO:2:

```
Phe  Lys  Gly  Thr  Pro  Thr  Ala  Glu  Asn  Pro  Glu  Tyr  Leu  Gly  Leu
1                   5                        10                       15
```

( 2 ) INFORMATION FOR SEQ ID NO:3:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: C-terminal ( x i ) SEQUENCE DESCRIPTION: SEQ ID NO:3:

```
Phe  Lys  Gly  Ser  Thr  Ala  Glu  Asn  Ala  Glu  Tyr  Leu  Arg  Val
1                   5                        10
```

( 2 ) INFORMATION FOR SEQ ID NO:4:

(i) SEQUENCE CHARACTERISTICS:
    (A) LENGTH: 11 amino acids
    (B) TYPE: amino acid
    (D) TOPOLOGY: linear (ii) MOLECULE TYPE: protein (iii) HYPOTHETICAL: NO (v) FRAGMENT TYPE: internal (xi) SEQUENCE DESCRIPTION: SEQ ID NO:4:

Ile Val Arg Lys Arg Thr Leu Arg Arg Leu Leu
1               5                   10

(2) INFORMATION FOR SEQ ID NO:5:

(i) SEQUENCE CHARACTERISTICS:
    (A) LENGTH: 11 amino acids
    (B) TYPE: amino acid
    (D) TOPOLOGY: linear (ii) MOLECULE TYPE: protein (iii) HYPOTHETICAL: NO (v) FRAGMENT TYPE: internal (xi) SEQUENCE DESCRIPTION: SEQ ID NO:5:

Lys Ile Arg Lys Tyr Thr Met Arg Arg Leu Leu
1               5                   10

(2) INFORMATION FOR SEQ ID NO:6:

(i) SEQUENCE CHARACTERISTICS:
    (A) LENGTH: 11 amino acids
    (B) TYPE: amino acid
    (D) TOPOLOGY: linear (ii) MOLECULE TYPE: protein (iii) HYPOTHETICAL: NO (v) FRAGMENT TYPE: internal (xi) SEQUENCE DESCRIPTION: SEQ ID NO:6:

Asn Asn Thr Ser Ser Ser Pro Gln Pro Lys Lys
1               5                   10

(2) INFORMATION FOR SEQ ID NO:7:

(i) SEQUENCE CHARACTERISTICS:
    (A) LENGTH: 12 amino acids
    (B) TYPE: amino acid
    (D) TOPOLOGY: linear (ii) MOLECULE TYPE: protein (iii) HYPOTHETICAL: NO (v) FRAGMENT TYPE: internal (xi) SEQUENCE DESCRIPTION: SEQ ID NO:7:

Ile Asn Gly Ser Pro Arg Thr Pro Arg Arg Gly Gln
1               5                   10

(2) INFORMATION FOR SEQ ID NO:8:

(i) SEQUENCE CHARACTERISTICS:
    (A) LENGTH: 9 amino acids
    (B) TYPE: amino acid (D) TOPOLOGY: linear (ii) MOLECULE TYPE: protein (iii) HYPOTHETICAL: NO (v) FRAGMENT TYPE: internal (xi) SEQUENCE DESCRIPTION: SEQ ID NO:8:

Arg Phe Thr Phe Ser Pro Gly Gln Asp
1               5

(2) INFORMATION FOR SEQ ID NO:9:

(i) SEQUENCE CHARACTERISTICS:
    (A) LENGTH: 17 amino acids
    (B) TYPE: amino acid
    (D) TOPOLOGY: linear (ii) MOLECULE TYPE: protein (iii) HYPOTHETICAL: NO (v) FRAGMENT TYPE: internal (xi) SEQUENCE DESCRIPTION: SEQ ID NO:9:

Gly Leu Ala Arg Asp Ile Met Arg Asp Ser Asn Tyr Ile Ser Lys Gly
1               5                   10                  15

Ser (2) INFORMATION FOR SEQ ID NO:10:

(i) SEQUENCE CHARACTERISTICS:
    (A) LENGTH: 17 amino acids
    (B) TYPE: amino acid
    (D) TOPOLOGY: linear (ii) MOLECULE TYPE: protein (iii) HYPOTHETICAL: NO (v) FRAGMENT TYPE: internal (xi) SEQUENCE DESCRIPTION: SEQ ID NO:10:

Gly Leu Ala Arg Asp Ile Met Asn Asp Ser Asn Tyr Ile Val Lys Gly
1               5                   10                  15

Asn (2) INFORMATION FOR SEQ ID NO:11:

(i) SEQUENCE CHARACTERISTICS:
    (A) LENGTH: 16 amino acids
    (B) TYPE: amino acid
    (D) TOPOLOGY: linear (ii) MOLECULE TYPE: protein (iii) HYPOTHETICAL: NO (v) FRAGMENT TYPE: internal (xi) SEQUENCE DESCRIPTION: SEQ ID NO:11:

Gly Leu Ala Arg Leu Ile Glu Asp Asn Glu Tyr Thr Ala Arg Gln Gly
1               5                   10                  15

ACTIVATION-STATE-SPECIFIC PHOSPHOPROTEIN IMMUNODETECTION

RELATED APPLICATIONS

This application is a continuation of application Ser. No. 07/918,370, filed Jul. 23, 1992, now abandoned, which is a continuation-in-part of Ser. No. 07/866,728, filed Apr. 10, 1992, now abandoned.

FIELD OF THE INVENTION

This invention relates to methods of detecting and distinguishing differentially activated gene products, including tyrosine kinases and proto-oncogene products.

Part of the work leading to this invention was made with United States Government funds. Therefore, the U.S. Government has certain rights in this invention.

BACKGROUND OF THE INVENTION

Treatment decisions for individual breast cancer patients are frequently based on the number of axillary lymph nodes involved with disease, estrogen receptor and progesterone receptor status, size of the primary tumor, and stage of disease at diagnosis (Tandon et al., J. Clin. Oncol. 7:1120–1128 (1989)). However, even with this variety of factors, it is not possible to predict accurately the course of disease for all breast cancer patients. There is clearly a need to identify new markers in order to separate patients with good prognosis, who will need no further therapy, from those whose cancer is more likely to recur and who might benefit from more intensive adjuvant treatments.

Some of the more promising candidates for new prognostic factors include proto-oncogenes which may be amplified, overexpressed, mutated or otherwise activated in malignant cells. Alterations of proto-oncogenes have been found in many forms of human tumors (Bishop, Science 235:305–311 (1987); Klein et al., Nature 315:190–195 (1985); Varmus, Ann. Rev. Genet., 18:553–612 (1984)). For one of these potentially transforming genes, the c-erbB-2 (HER-2, neu) gene, amplification was shown to be a strong prognostic factor in primary human breast cancers; patients with amplified c-erbB-2 had shorter disease-free and overall survival than patients with no amplification (Slamon et al., Science 235:177–182 (1987); Varley et al., Oncogene 1:423–439 (1987)).

Expression of the c-erbB-2 oncogene protein itself has also been examined for its prognostic potential in both node-positive and node-negative breast cancer. In node-positive patients already known to be at high risk of recurrence, overexpression of c-erbB-2 at the protein level has been consistently associated with shorter disease-free and overall survival. In node-negative patients, however, where improved prognostic prediction has far greater therapeutic implications, c-erbB-2 receptor expression has failed to predict disease outcome in numerous studies (Slamon et al., Science 235:177–182 (1987); Borg et al., Cancer Res. 50:4332–4337 (1990); Paterson et al., Cancer Res. 51:556–567 (1991)). Hence, a more accurate method for characterizing the biological significance of receptor overexpression in node-negative disease could provide clinical dividends.

Recently, the wild-type c-erbB-2 receptor has been shown to exist in two interconvertible forms, p175 and p185 (Epstein et al., J. Biol. Chem. 265:10746–10751 (1990)). The p175/c-erbB-2 receptor isoform exhibits enhanced in vitro tyrosine kinase activity, receptor-specific phosphotyrosine content, and electrophoretic mobility when compared with the p185 isoform. Using conventional single-step c-erbB-2 immunodetection assays, however, tyrosine-phosphorylated p175 and serine/threonine-phosphorylated p185 may be technically indistinguishable.

Only the activated form of a tyrosine kinase is likely to influence cell growth and differentiation. Clinical inconsistencies regarding the role of c-erbB-2 in breast cancer could reflect heterogeneity of receptor activation in vivo. A simple antibody-based method which would distinguish the kinase-active form of c-erbB-2 (arising, for example, due to autocrine or paracrine loops, or receptor mutations) from the inert kinasein-active configuration could provide valuable biological and clinical information.

Moreover, the pharmaceutical industry is interested in evaluating pharmaceutically useful compounds which act as growth factor agonists or antagonists. Tens of thousands of compounds per year need to be tested in an entry level or "high flux" screening protocol. Out of the thousands of compounds scrutinized, one or two will show some activity in the entry level assay. These compounds are then chosen for further development and testing. Ideally, a screening protocol would be automated to handle many samples at once, and would not use radioisotopes or other chemicals that pose safety or disposal problems. An antibody-based approach to evaluating drug growth factor activities would provide these advantages and offer the added advantage of high selectivity.

Activation-specific receptor antibodies have been isolated by other investigators pursuing a variety of experimental studies. However, these isolations appear to have been at least partly serendipitous, and the procedures employed do not provide a systematic approach to this task. Keating et al. (J. Biol. Chem. 263:12805–12808 (1988)) raised polyclonal antibodies to an unphosphorylated peptide corresponding to residues 934–951 of the C-terminal region of the PDGF receptor and subsequently demonstrated that this antiserum recognized the native (immunoprecipitated) but not denatured (immunoblotted) activated PDGF receptor. Keating concluded that ligand-inducible tyrosine kinase activation is associated with a conformational change in the receptor which somehow enables antibody binding. Similarly, Downing et al. (Mol. Cell. Biol. 11:2489–2495 (1991)) raised polyclonal antibodies to an unphosphorylated juxtamembrane domain sequence (552–574) of the CSF-1 receptor. This antiserum also exhibited specificity for the immunoprecipitated (but not denatured) activated receptor isoform, theoretically consistent with conformational change mediated by phosphatidylinositol 3-kinase binding to this region. Campos-Gonzalez and Glenney (Growth Factors 4:305–316 (1991)) isolated a monoclonal antibody, raised against intact receptor, that recognized both the native and denatured form of the EGF receptor. However, the antiserum also recognized EGF receptors lacking the three major tyrosine autophosphorylation sites while failing to recognize $^{32}$P-labelled tryptic peptides; hence, it was proposed that the antibody recognizes a phosphorylation-dependent conformational change which partially renatures following SDS denaturation for immunoblotting. A similar approach using intact proteins as immunogens for monoclonal antibody production was adopted by Hu et al. (Mol. Cell. Biol. 11:5792–5799 (1991)). These workers developed a wide range of monoclonal antibodies to the retinoblastoma (Rb) gene product, some of which distinguished under- and unphosphorylated isoforms of this protein. Gullick et al. (EMBO J. 4:2869–2877 (1985)) prepared antisera to the autophosphorylation sites of the EGF receptor using unphosphorylated peptides, but the resulting antibodies did not distinguish activated and inactivated receptor isoforms. Antibodies directed against phosphotyrosine have also been used in attempts to distinguish activated and inactivated receptor subtypes (Wang, Mol. Cell. Biol. 5:3640–3643 (1985); Wildenhain et al., Oncogene 5:879–883 (1990)), but such antibodies are not receptor-specific. The resulting data are therefore difficult to interpret: tyrosine-phosphorylated bands with electrophoretic mobility between 160 and 190 kilodaltons, for example, could represent activation of the c-erbB-2 receptor, but could also indicate activation of receptors for epidermal growth factor, fibroblast growth factors or platelet-derived growth factor (compare, for example, the electrophoretic mobility of c-erbB-2 and PDGF receptors in FIGS. 4 and 6, Epstein et al., Cell Growth and Differentiation, 3:157–164 (1992)).

SUMMARY OF THE INVENTION

The invention generally features antibody reactive specifically with one of the two isoforms of a reversibly phosphorylated protein and not reactive with either the other isoform of the protein or with similarly modified (phosphorylated or unphosphorylated) forms of different proteins. Also featured are methods for producing the activation-state-specific and protein-specific antibodies, kits including the antibodies for use in characterizing the activation state of a protein, and methods for evaluating the agonist or antagonist activity of pharmaceutically useful compounds towards the conversion of a specific protein from its inactive to its active state.

In brief, the method exploits synthetic phosphopeptides incorporating informative protein phosphorylation sites. These peptides are used as immunogens to develop antibodies which indicate the activation state of tyrosine kinases and other proteins phosphorylated on serine or threonine residues.

The antibodies of the invention have wide applicability in both clinical and laboratory research. The described technology is relevant to the production of activation-state-specific immunodetection reagents for a wide range of regulatory proteins relevant to human health and disease.

Other features and advantages of the invention will be apparent from the following description of the preferred embodiments thereof and from the claims.

DESCRIPTION OF THE PREFERRED EMBODIMENTS

Here we describe the development of high-specificity antibodies against the active form of the wild-type c-erbB-2 receptor, p175, using a technique which we have termed activation-specific phosphoprotein immunodetection, or APHID.

To apply this technique, tyrosine-phosphorylated peptides corresponding to the major tyrosine autophosphorylation site of the c-erbB-2 receptor, C-terminal amino acids 1243–1255 (Akiyama et al., Mol. Cell. Biol., 11:838–842 (1991)), were synthesized, coupled (via an amino terminal cysteine residue) to a carrier protein (hemocyanin), combined with adjuvant and inoculated into rabbits. Following raising of polyclonal antisera, antibodies to the tyrosine-phosphorylated peptide were purified in a reverse-purification process by adsorption of non-activation-specific antibodies to an unphosphorylated peptide of the same sequence. Where necessary, contaminating non-receptor-specific antiphosphotyrosine antibodies were removed by adsorption to phosphotyramine.

APHID technology is generally applicable to the identification of protein isoforms characterized by varying phosphorylation states. A typical scheme for preparing polyclonal antibodies for activation-state-specific phosphoprotein immunodetection is the following.

Figure 1:
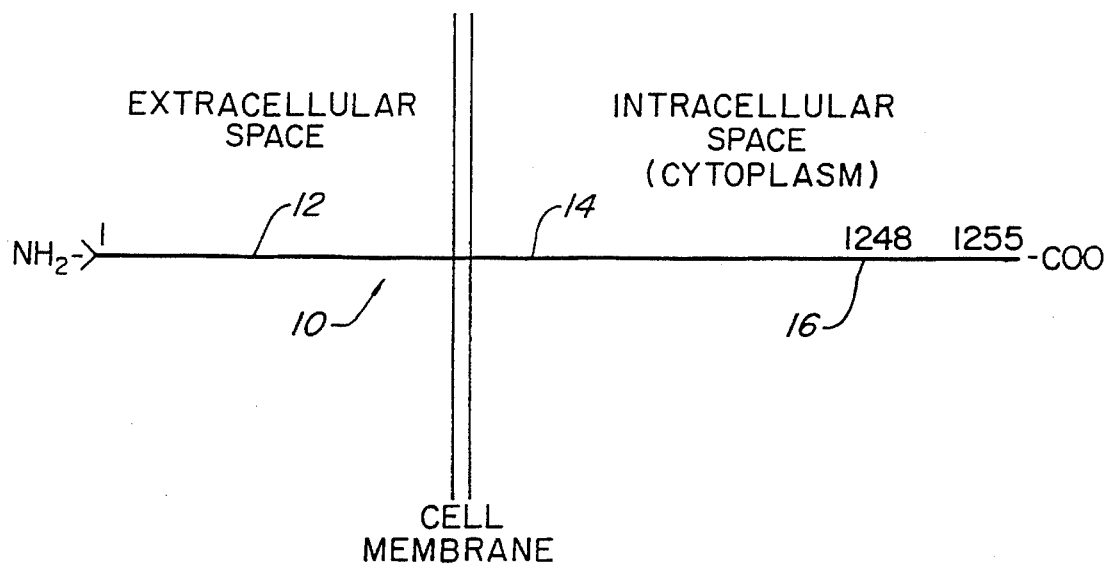
FIG. 1 is a schematic diagram of the c-erbB-2 receptor.
Figure 2:
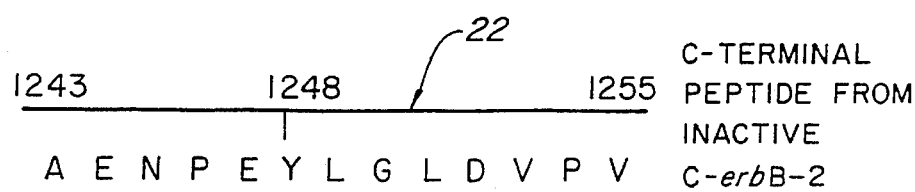
FIG. 2 is a representation (SEQ ID NO:1) of the two c-erbB-2 C-terminal peptides synthesized, one of which is a phosphopeptide.
Figure 2:
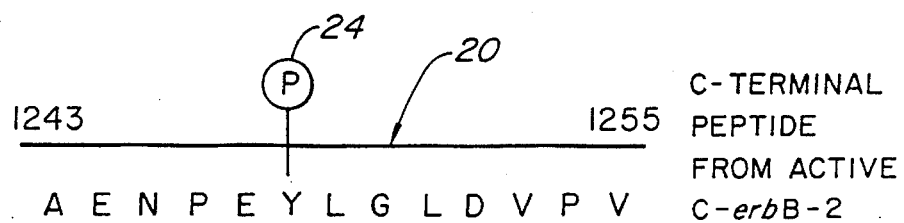

Referring to FIG. 1, the c-erbB-2 receptor 10 consists of an N-terminal, extracellular domain 12 and a C-terminal, intracellular domain 14. A prime autophosphorylation site in the receptor 10 is the C-terminal tyrosine at amino acid residue 1248 (16). Referring to FIG. 2, to prepare high-specificity antibodies, tyrosine-phosphorylated peptides 20, corresponding to the C-terminal region of activated c-erbB-2, from amino acid residues 1243–1255, were synthesized, as will be described in more detail below, and used with adjuvant to immunize rabbits. Antibodies directed against both the phosphorylated tyrosine residue (PTyr) 24, referred to as Y-P, and flanking amino acids should be both activation-specific and receptor-specific.

Figure 3A:
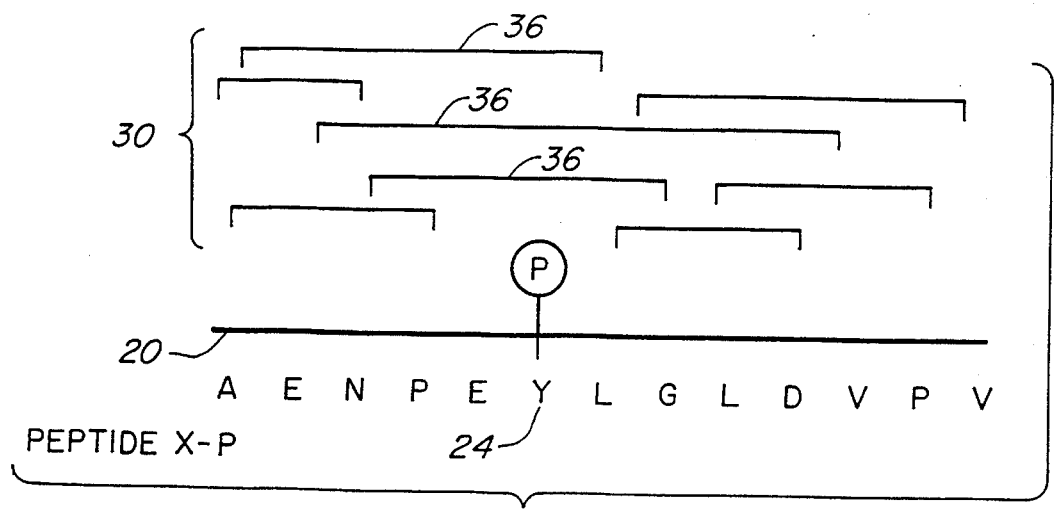
FIGS. 3a and 3b show reverse-immunoaffinity purification of polyclonal antisera raised against the c-erbB-2 sequence 1243–1255 (SEQ ID NO:1), containing a phosphorylated tyrosine residue.

The antibodies of interest were purified according to the following isolation scheme. Referring to FIG. 3a, crude antisera collected from immunized rabbits contains polyclonal antibodies 30 raised against the immunogen 20 (peptide X-P). Some of the antibodies 36 in the antisera recognize an epitope that includes the phosphorylated tyrosine (PTyr) residue 24 and would, therefore, be specific for the activated form of the c-erbB-2 receptors. Others recognize epitopes that do not include the PTyr residue 24 and must be removed from the antibody population.

Figure 3B:
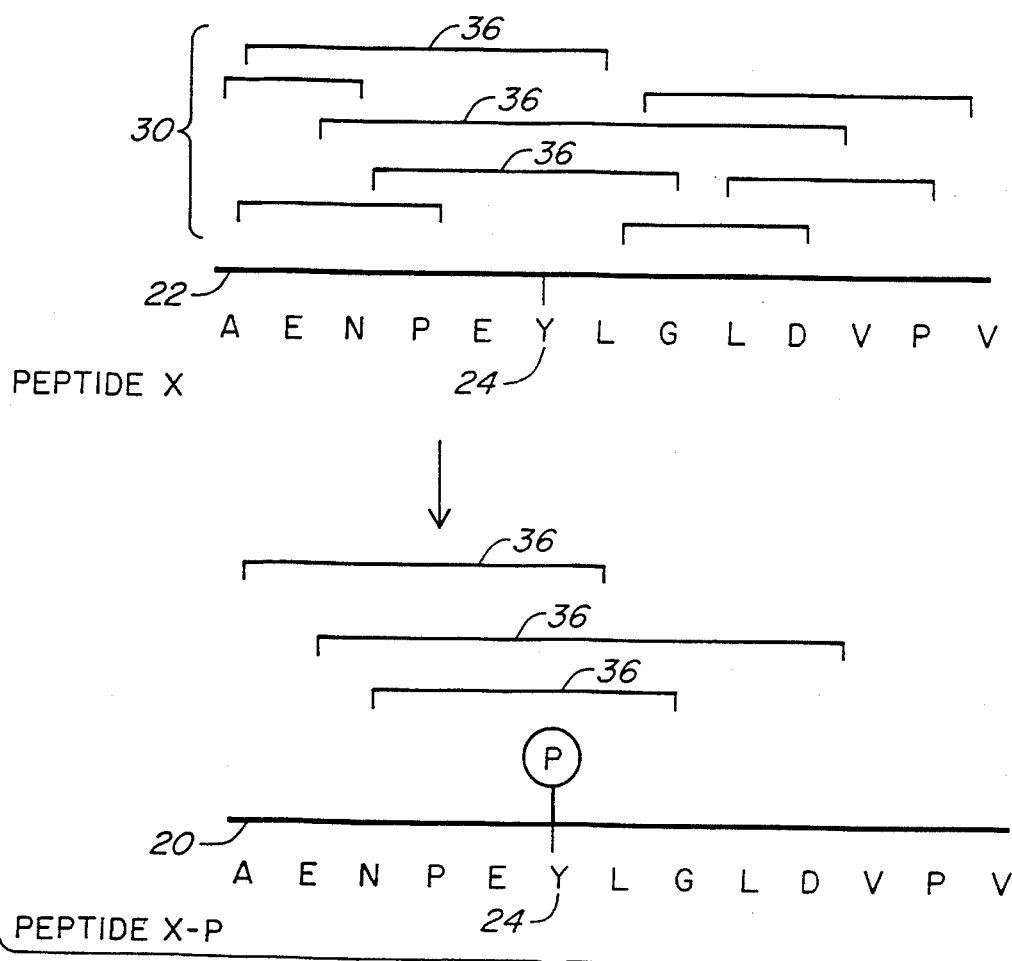

Referring to FIG. 3b, the crude antiserum containing polyclonal antibodies 30 is purified by reverse immunoaffinity purification using the unphosphorylated peptide-X 22 attached to chromatography beads to remove those antibodies that are non-PTyr specific. The isolated antisera contains only activation-specific antiphosphoprotein (apt) antibodies 36 specifically recognizing PTyr-containing sequences 20.

Figure 4A:
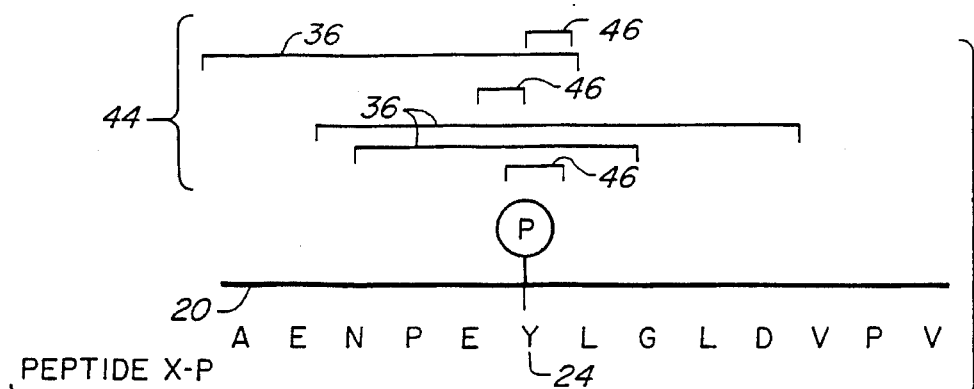
FIGS. 4a and 4b show reverse-immunoaffinity purification of the polyclonal antisera of FIGS. 3a and 3b from contaminating non-protein-specific antiphosphotyrosine antibodies.
Figure 4B:
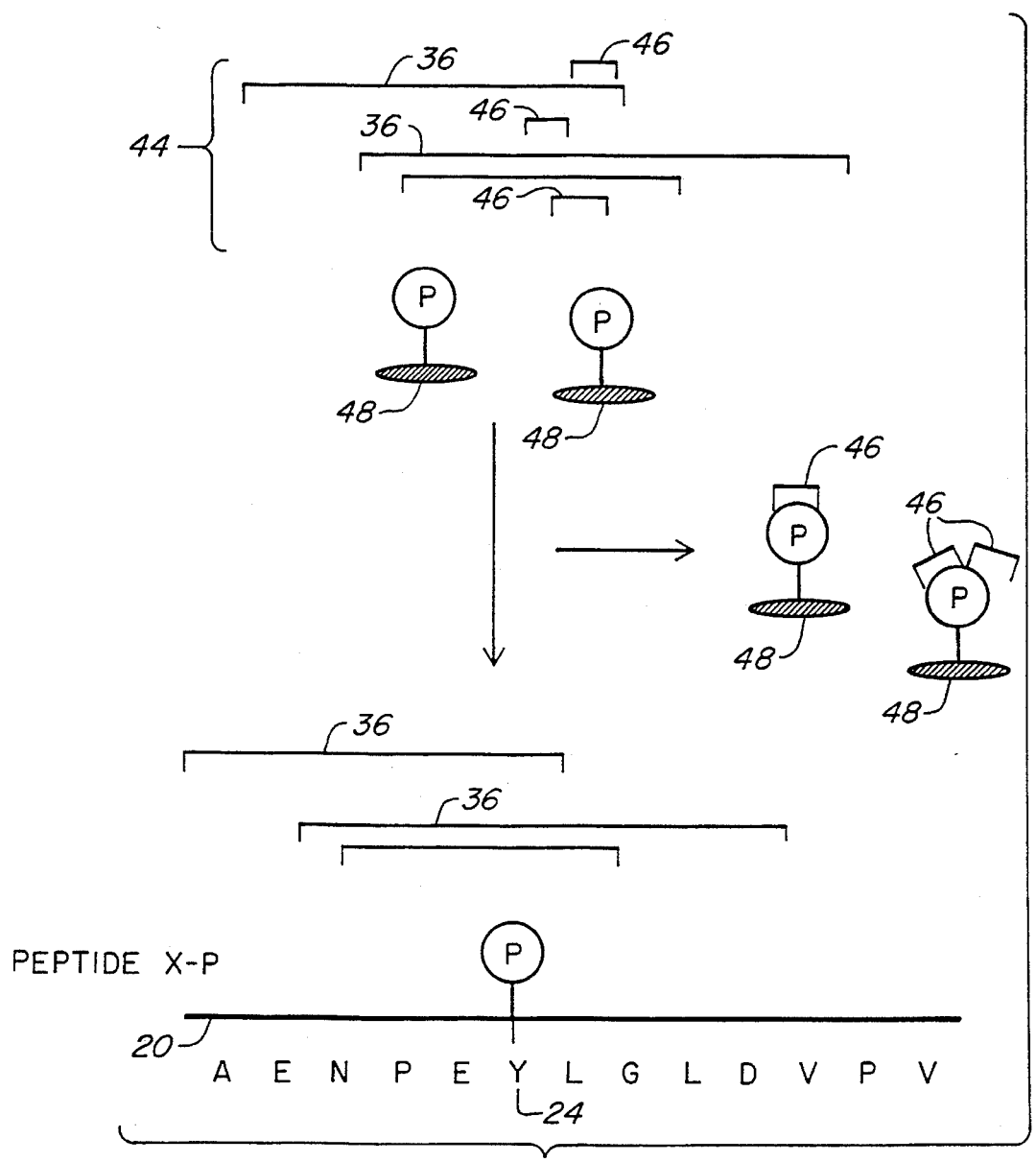

In some animals the immunogen 20 may have raised non-receptor-specific antiphosphotyrosine antibodies. These sera would need an additional purification step. Referring to FIG. 4a, antibody population 44, purified by one-step reverse immunopurification using non-phosphorylated peptide 22, contains some non-receptor-specific antibodies 46 recognizing an epitope that does not overlap onto amino acid residues flanking PTyr 24. Referring also to FIG. 4b, antiserum 44 is, then, immunoaffinity purified over phosphotyramine-linked beads 48 to remove non-receptor-specific antibodies, leaving antiserum containing only activation-specific and receptor-specific antibodies 36, directed against the activated form of the c-erbB-2 receptor.

The methodology of activation-state-specific phosphoprotein immunodetection, or APHID, as described above, can prove useful for identifying tyrosine kinase receptors which are activated (either by structural mutations or by autocrine ligand production) in human tumors, a distinction which could prove to have prognostic and therapeutic significance. With minor adaptations, the APHID approach should prove valuable, in addition, for a wide variety of other clinical and experimental applications.

Figure 5:
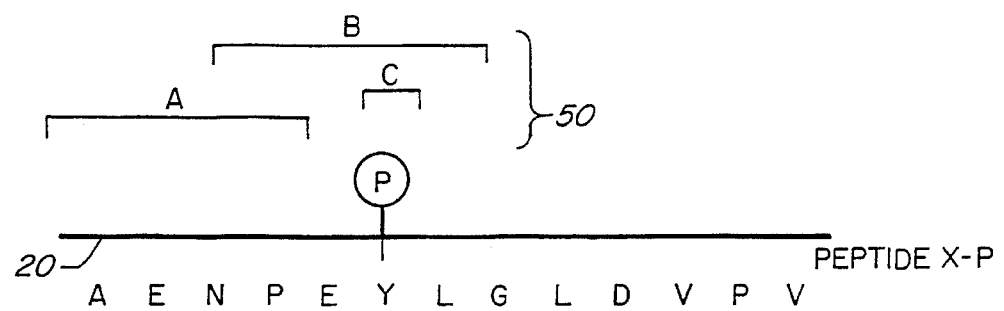
FIG. 5 shows a screening strategy for isolating monoclonal antibodies recognizing phosphorylated residues within specific protein sequences.
Figure 5:
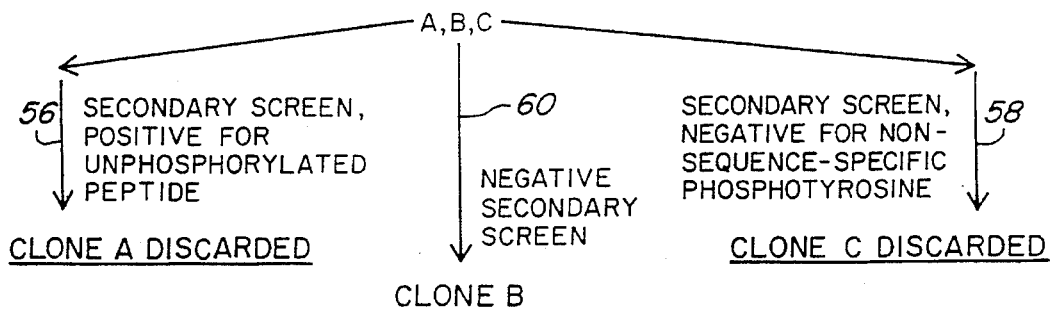
Figure 5:
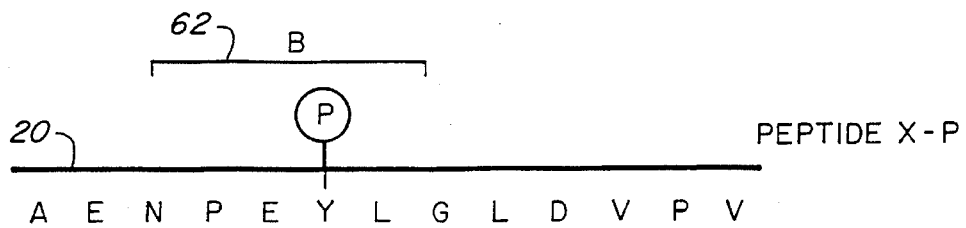

For example, activation-specific monoclonal antibodies (mAb) could be raised against synthetic phosphopeptides, such as the 1243–1255 c-erbB-2 phosphopeptide used above. This is a minor adaptation of the technique since the polyclonal APHID antibody preparations are, in reality, no more than a mixture of multiple monoclonal antibodies. A hybridoma cell line producing a monoclonal APHID antibody would, however, provide an inexhaustible source of uniform quality antibodies. Production of activation-state-specific monoclonal antibodies does not require reverse immunoaffinity purification, but does involve a similarly sophisticated clonal screening strategy. Referring to FIG. 5, monoclonal antiphosphopeptide (apt antibodies 50 are raised against the 1243–1255 c-erbB-2 phosphotyrosine (PTyr)-containing phosphopeptide 20. Hybridoma supernatants are initially screened 54 using the immunogen 20 in a phosphopeptide-based ELISA, which results in the isolation of positive clones A, B, and C, expressing the 50A, 50B, and 50C mAb. A series of secondary screens is used next. One screen 56 indicates that clone A is also positive for the unphosphorylated peptide, presumably reflecting affinity to a peptide sequence lateral to the phosphorylated moiety; therefore, clone A is discarded as not being activation-specific. In another secondary screen 58, clone C is shown to be positive for a non-sequence-specific phosphotyrosine; therefore, it also is discarded. Clone B is negative 60 in all secondary screens and, therefore, is selected as an activation-specific and protein-specific apt monoclonal antibody 62.

In addition, polyclonal antisera could be obtained by the reverse-immunoaffinity purification procedure, but by using synthetic phosphopeptides as purification rather than immunization reagents. This approach would enable production of antibodies specifically recognizing unphosphorylated peptide sequences in situations where such sequences are of special interest either in their own right (for example, where an inactivated protein may be sought, or where protein activation correlates with dephosphorylation of a specific residue; see below) or as controls or comparisons for immunodetection of phosphorylated protein species.

Figure 6A:
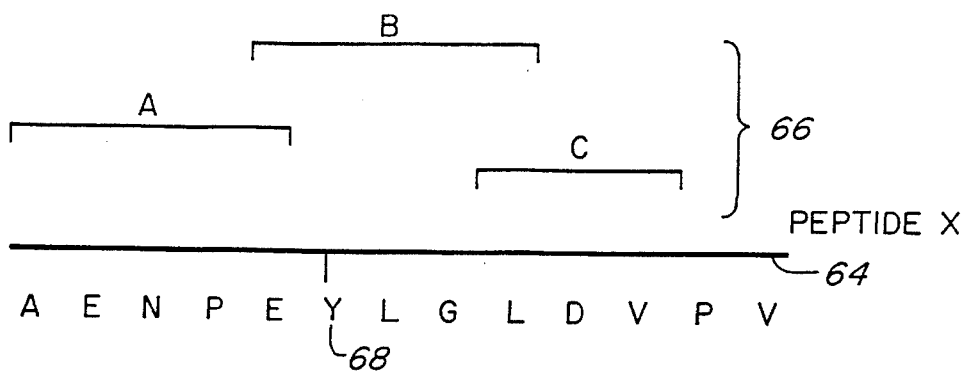
FIGS. 6a and 6b show the use of phosphopeptides as reverse-immunoaffinity purification reagents for preparing polyclonal antisera recognizing only the unphosphorylated protein sequence.

Referring to FIG. 6a, crude antisera collected from rabbits immunized with peptide-X 64, which is non-phosphorylated, contains polyclonal antibodies A, B, and C 66. Antibody B recognizes an epitope that includes the non-phosphorylated tyrosine residue 68 and would, therefore, be specific for the unphosphorylated form of protein-X 64. Antibodies A and C, on the other hand, recognize epitopes that do not include the tyrosine residue 68 and would, therefore, fail to distinguish differentially phosphorylated forms of this protein.

Figure 6B:
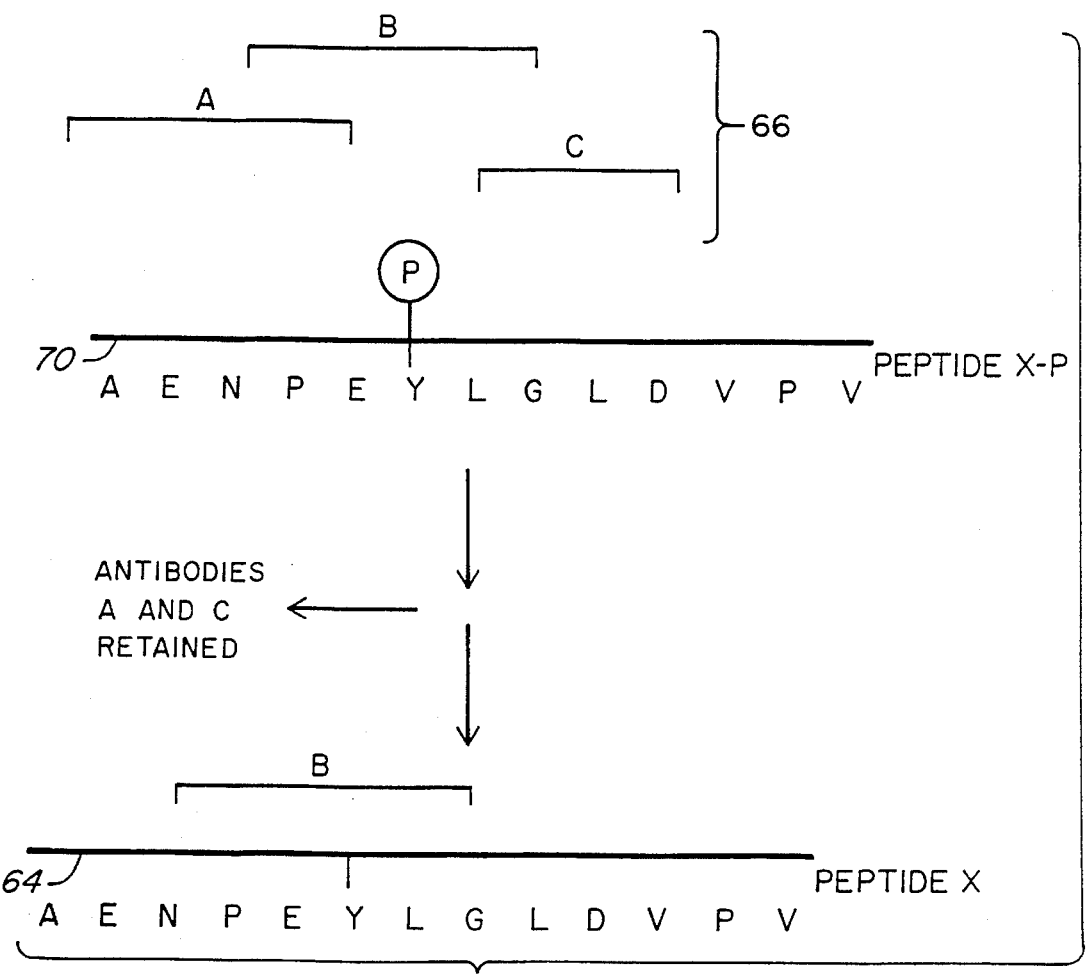

Referring to FIG. 6b, the crude antisera containing polyclonal antibodies 66 is purified by reverse immunoaffinity purification over the phosphorylated peptide X-P 70 attached to a solid support such as agarose beads. Antibodies A and C are retained on the beads, and the isolated antiserum contains only antibodies B specifically recognizing non-phosphorylated tyrosine-containing sequences 64.

Depending upon whether phosphorylation or dephosphorylation of a specific residue is associated with the desired activation state, the above strategies may be applied to detect not only activated, but also inactivated, protein isoforms.

In another approach, polyclonal antisera raised against multiple phosphopeptides (or dephosphopeptides) would be expected to provide increased sensitivity of detection (when positive) for proteins containing more than one critical phosphorylation site, as well as improved specificity (when negative). This strategy could be used to generate highly sensitive activation- and inactivation-specific antibodies for protein isoform quantification. For example, the epidermal growth factor (EGF) receptor contains at least four tyrosine autophosphorylation sites (Margolis et al., J. Biol. Chem. 264:10667–10671 (1989)). Hence, simultaneous use of such peptides (phosphorylated or unphosphorylated) in combination as either immunogens or purification reagents would be expected to increase the sensitivity and specificity of activation-state-specific protein detection.

Tyrosine-phosphorylated sequences provide only one type of post-translational modification by phosphorylation; the other major residues phosphorylated within regulatory proteins are serines and threonines. In structural terms, serine/threonine phosphorylation is highly analogous to tyrosine phosphorylation. Hence, immunodetection of reversible phosphorylation at serine or threonine residues using the APHID technique should provide similarly valuable information. For example, Ser-315 in the p53 cell-cycle regulatory protein is phosphorylated in association with cell-cycle progression (Bischoff et al., Proc. Natl. Acad. Sci. USA, 87:4766–4770 (1990)). Detection of this modification could thus prove useful as a marker of early breast neoplasia. Similarly, Thr-686 in the c-erbB-2 receptor represents the major protein kinase C phosphorylation site of this protein; detection of this modification could provide useful information in studies of growth factor interactions in vitro and in vivo, and may also provide a marker for quantifying inactivated receptor expression in human tumor specimens. The functional significance of such reversible modifications may vary in different proteins, with some proteins being activated/inactivated by reversible phosphorylation of serine or threonine, and others by modification of tyrosine.

Antibodies may be raised that are directed against other members of the structurally related protein kinase molecular superfamily. Tyrosine kinases (which include both receptor and non-receptor kinases) exhibit major structural and functional homology (Hanks et al., Science, 241:42–52 (1988)).

Figure 7:
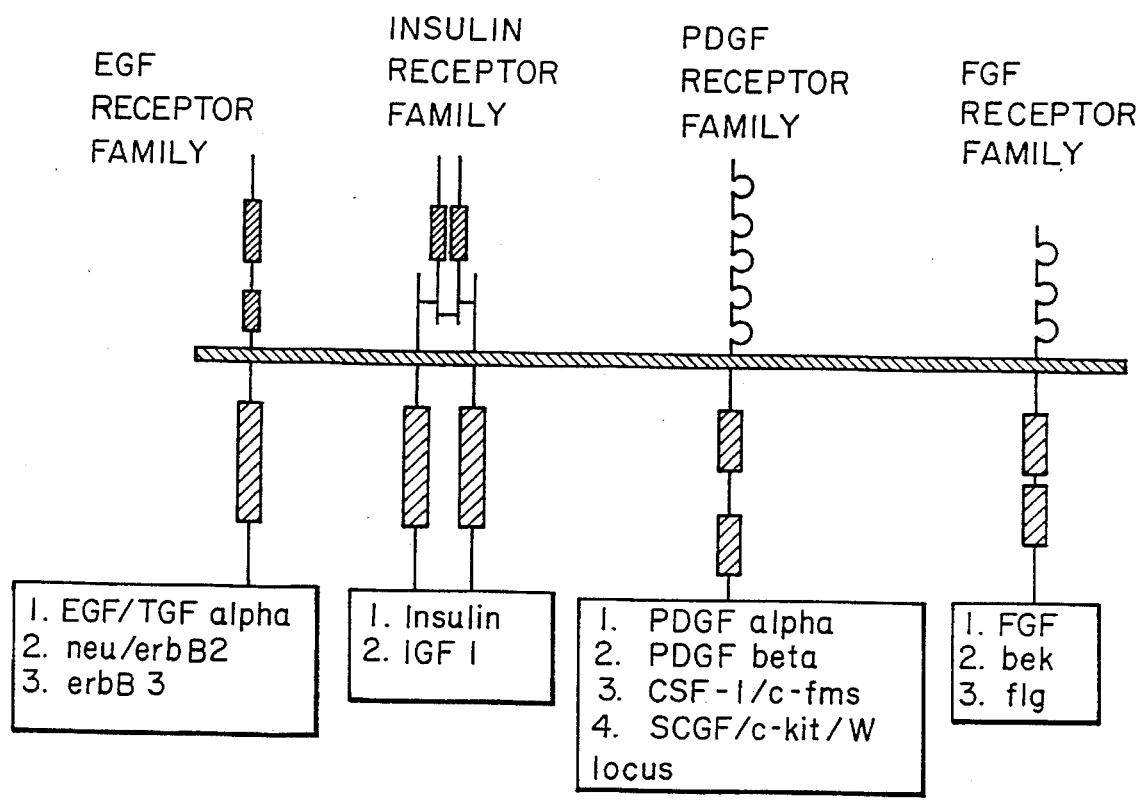
FIG. 7 is a schematic representation of some of the evolutionarily-conserved subfamilies of the receptor tyrosine kinase superfamily.
Figure 8A:
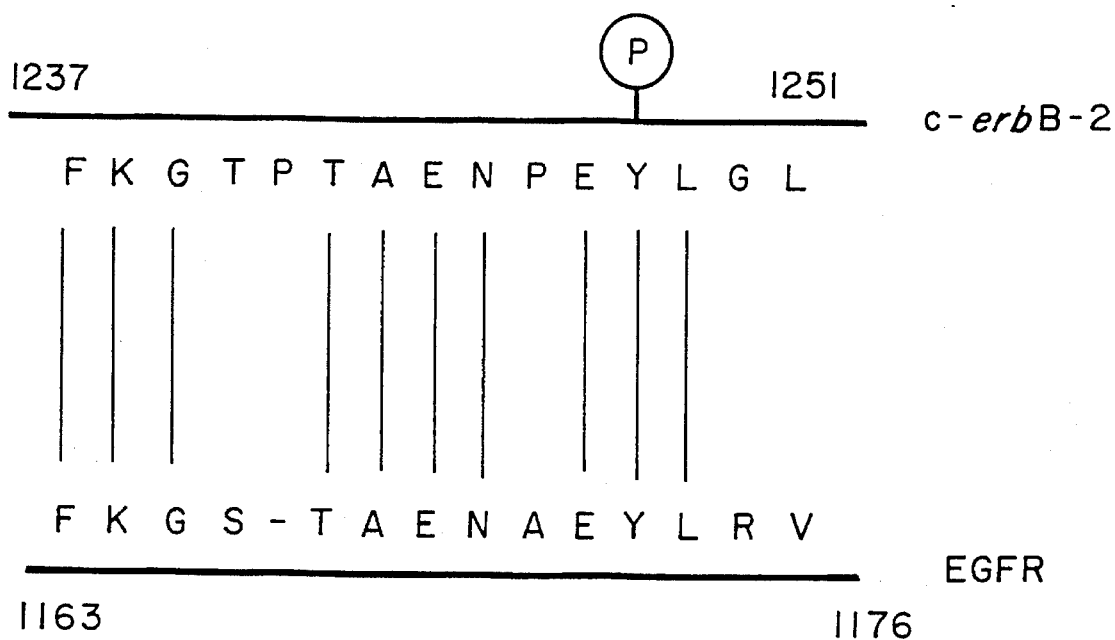
FIGS. 8a and 8b show comparative amino acid sequences of major tyrosine-containing and threonine-containing autophosphorylation sequences within both the C-terminal (FIG. 8a SEQ ID NO:2 and SEQ ID NO:3) and juxtamembrane (FIG. 8b SEQ ID NO:4 and SEQ ID NO:5) domains of the EGF receptor and c-erbB-2 molecule respectively.
Figure 8B:
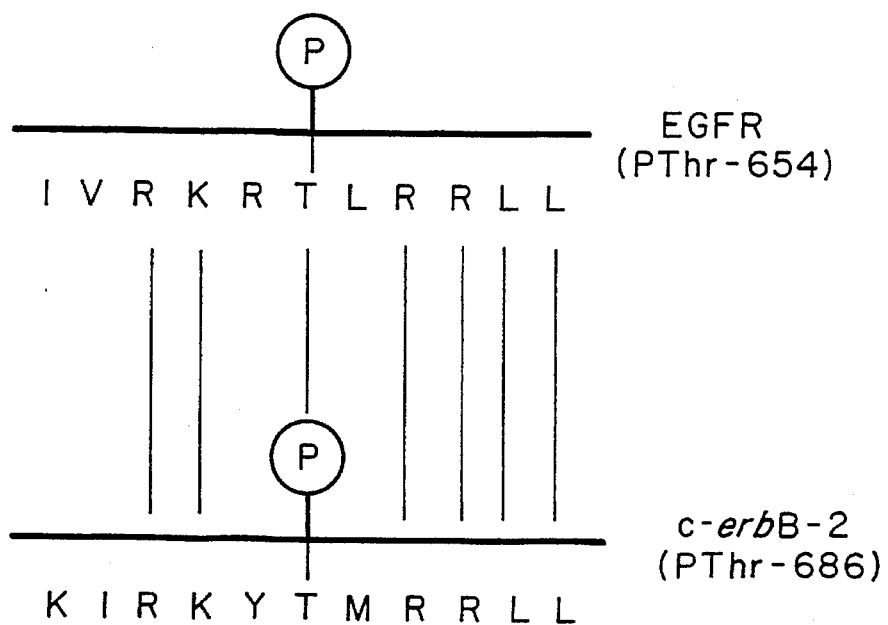

Referring to FIG. 7, some of the members of the receptor tyrosine kinase superfamily are shown in schematic representation. The epidermal growth factor receptor (EGFR) family includes c-erbB-2, c-erbB-3, and EGF receptor. The platelet-derived growth factor (PDGF) receptor family is represented by platelet-derived growth factor receptors alpha and beta (PDGFR alpha and PDGFR beta), colony stimulating factor-1 receptor (CSF-1R) and the stem cell growth factor receptor (also known as the c-kit gene product and the W locus gene product). A set of receptors for the fibroblast growth factor family is structurally somewhat similar to the PDGF receptor family. By contrast, members of the insulin receptor family (including the receptor for insulin and the receptor for insulin-like growth factor 1) display a radically different, heterotetrameric configuration. In the schematic shown in FIG. 7, filled rectangles indicate the approximate position of the intracellular tyrosine kinase (catalytic) domains, which make up one of the structurally homologous modules shared between these ancestrally-derived molecules. Referring to FIG. 8a, the comparative amino acid sequences of the C-terminal EGF receptor and c-erbB-2 receptor autophosphorylation sequences are given, showing the striking sequence homology of the respective tyrosine autophosphorylation sites. FIG. 8b shows a similar degree of sequence homology between the juxtamembrane domain of these two receptors, including the major protein kinase C threonine-phosphorylation sites.

The striking extent of structural and functional homology within these evolutionarily-related molecules indicates that the activation-state-specific immunodetection approach should prove readily applicable to other tyrosine kinases (and also to protein phosphorylated on serine or threonine). For example, the activity of the c-src (non-receptor tyrosine kinase) protein is critically dependent upon differential phosphorylation of Tyr-416 and Tyr-527 (Yarden et al., Nature 323:226–232 (1986); Hunter, Cell 49:1–4 (1987); Cobb et al., Mol. Cell. Biol. 11:5832–5838 (1991)). Antibodies directed against this phosphopeptide sequence should thus be able to distinguish different activation states of the src molecule.

Phosphorylation of tyrosine or serine/threonine is a ubiquitous mechanism of protein activity regulation which is not confined to protein kinases. APHID methodology would therefore prove applicable to distinguishing differentially phosphorylated isoforms not only of protein kinases, but also of many other phosphoproteins. The p53 cell-cycle regulator (Bischoff et al., Proc. Natl. Acad. Sci. USA, 87:4766–4770 (1990)), the functionally related retinoblastoma (Rb) tumor suppressor gene product (Lees et al., EMBO J., 10:4279–4290 (1991)), and the nuclear steroid hormone receptor family (Denner et al., Science, 250:1740–1743 (1990); Kemppainen et al., J. Biol. Chem., 267:968–974 (1992)) are some of the important cellular proteins known to regulate their activity by reversible phosphorylation.

Figure 9:
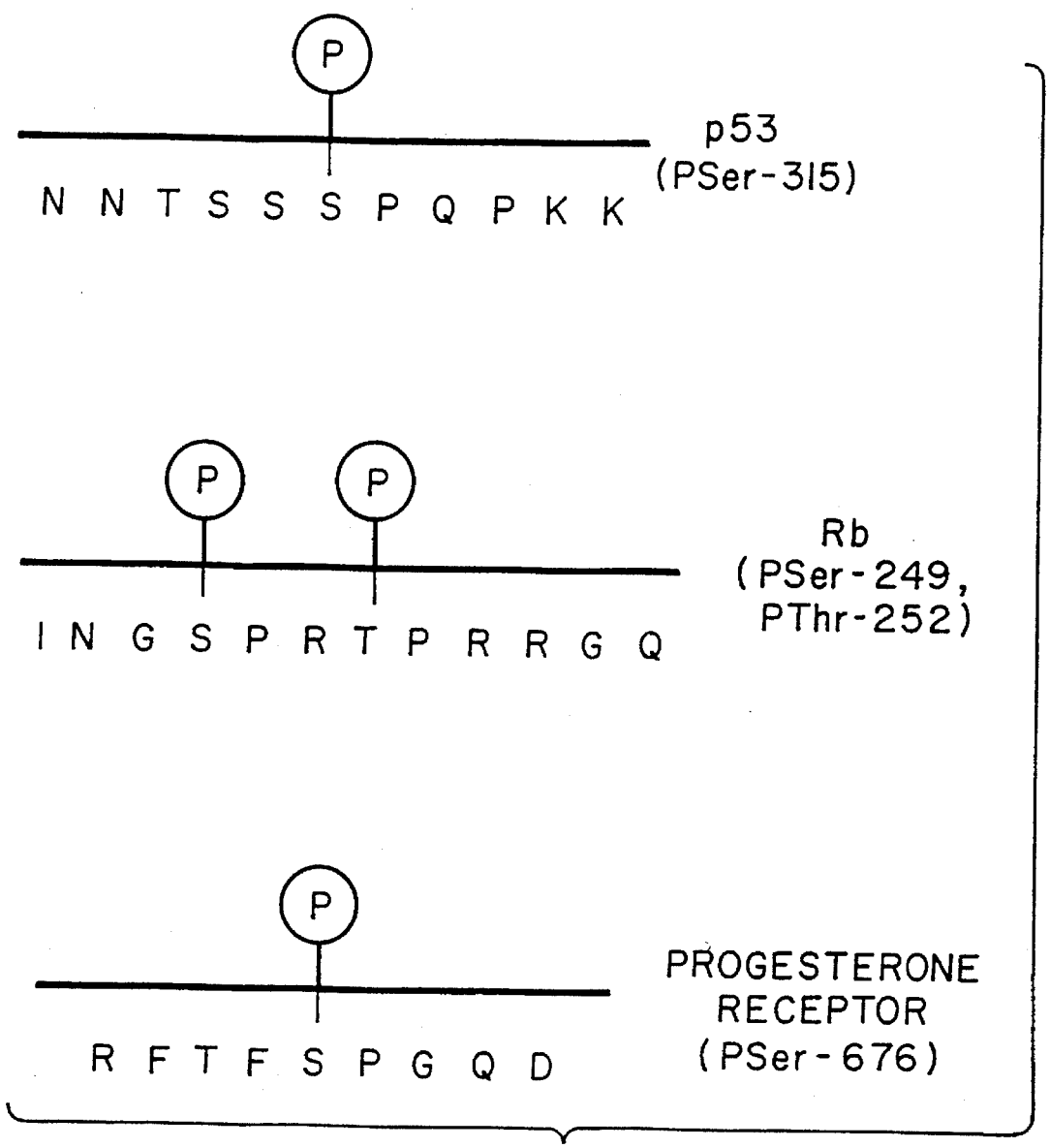
FIG. 9 shows serine- and threonine-containing phosphorylation sites within the p53 (SEQ ID NO:6), retinoblastoma (Rb) (SEQ ID NO:7), and progesterone receptor (SEQ ID NO:8) proteins.

Referring to FIG. 9, the p53 cell-cycle control molecule is reversibly phosphorylated on serine-315 to give the inactive species when cells commence proliferation through the cell-cycle. Another cell-cycle control protein, the retinoblastoma (Rb) molecule, is simultaneously phosphorylated on two closely-associated residues, Ser-249 and Thr-252, during cell-cycle modulation (Lees et al., EMBO J. 10:5279–4290 (1991)). Similarly, human progesterone receptor (hPR)—a member of the nuclear steroid hormone receptor superfamily which includes the receptors for estrogen, glucocorticoids, mineralocorticoids, androgens, vitamin D, retinoic acid and thyroid hormone (T3)—is reversibly phosphorylated on serine 676 following ligand activation (Denner et al., Science, 250:1740–1743 (1990)). APHID technology, as described, can be used to generate activation- and inactivation-specific antibodies against all such phosphoprotein species.

The following examples are presented to illustrate the advantages of the present invention and to assist one of ordinary skill in making and using the same. These examples are not intended in any way otherwise to limit the scope of the disclosure.

EXAMPLE I

Isolation of High Specificity Antibodies Against the Active Form of the c-erbB-2 Receptor Synthesis of tyrosine-phosphorylated peptides A major autophosphorylation site of the c-erbB-2 receptor expressed in NIH 3T3 cells is Tyr-1248 (Akiyama et al., Mol. Cell Biol., 11:833–842 (1991); Hazan et al., Cell Growth Differentiation, 1:3–7 (1990); Margolis et al., J. Biol. Chem., 264:10667–10671 (1989)). The C-terminal 1243–1255 c-erbB-2 peptide sequence, situated at the extreme C-terminal end of the receptor beyond the kinase domain, was synthesized in association with an N-terminal cysteine. Instead of incorporating a tyrosine residue at position 1248, however, a phosphorylated peptide was synthesized by standard Merrifield solid phase synthesis procedures using the t-boc strategy. The synthesis was performed on an ABI 430 peptide synthesizer using small scale (0.1 mmole) rapid cycles. The phosphotyrosine was incorporated as tert-butyoxycarbonyl-O-(dibenzyl)phosphono-L-tyrosine which was purchased from Peninsula Laboratories (Belmont, Calif.). The fully protected peptide was deprotected and cleaved from the phenylacetamidomethyl resin using trifluoromethane sulfonic acid. Reverse phase analysis of the crude peptide was achieved on a Vydac C-18 5 micron column 250 mm ×2.1 mm. A linear gradient from 0 to 60 min was run with 0.1% trifluoroacetic acid (TFA) and 0.09% TFA in acetonitrile. Amino acid analysis was performed using standard Pico-Tag procedures. Hydrolysis was carried out with 6N HCl at 145° C. for 2 hours. Composition analysis showed an almost complete conversion of phosphotyrosine to tyrosine due to the hydrolysis condition. To show that phosphotyrosine was indeed incorporated into the peptide, sequence analysis was performed using an ABI 477 gas phase sequenator. The presence of a phosphotyrosine residue was determined by the lack of signal at the expected cycle (since phosphotyrosine is not extracted by the solvents used) and the re-emergence of the expected sequence on subsequent cycles.

A non-phosphorylated cysteine-linked 1243–1255 peptide was also synthesized.

B104-1-1 cells expressing the constitutively activated c-erbB-2 transmembrane mutant (Weiner et al., Nature, 339:230–231 (1989)) were lysed and immunoprecipitated using antiphosphotyrosine antibodies. Preincubation of antiphosphotyrosine with either the PTyr-containing peptide or the peptide coupled to activated keyhole limpet hemocyanin antagonized c-erbB-2 immunoprecipitation at least as efficiently as 1 mM phosphotyrosine. These data indicate successful incorporation of phosphotyrosine into the synthetic peptide moiety.

Antibody isolation and purification

Cysteine-linked peptides corresponding to the C-terminal domain c-erbB-2 peptide sequence 1243–1255, and containing phosphorylated Tyr-1248, were coupled to activated keyhole limpet hemocyanin (KLH; Pierce Chemical Co., Rockford, Ill.). The peptide-KLH conjugate was then gel-purified and the fractions identified at $OD_{280}$. Incomplete Freund's adjuvant was mixed with the conjugate and the immunogen stored as aliquots at −20° C. until ready for use. Rabbits were inoculated at approximately 4–6 week intervals. Antisera were collected in 20–40 ml amounts beginning one week post-boost.

To establish the feasibility of chromatographic reverse purification of the crude antiphosphopeptide (apt) antiserum, immunoblotting of c-erbB-2-containing lysates was carried out after preincubating antibody solutions with various peptides. PTyr-1248-containing peptides antagonized apt binding to c-erbB-2 in SK-Br-3 human breast cancer cells more efficiently than did the unphosphorylated 1243–1255 peptide, while a juxtamembrane domain-derived peptide (Thr peptide) had no effect. In G8/DHFR lysates, addition of unphosphorylated peptide virtually abolished immunoreactivity of commercially available anti-erbB-2 antibodies raised against this unphosphorylated (p185) sequence, while apt-p175 binding remained strong. Near monospecificity of apt-175 binding was similarly apparent following single-step chromatographic reverse purification of crude apt antisera.

Purification of antisera, therefore, was undertaken by first coupling the non-phosphorylated cysteine-linked 1243–1255 peptide to Affigel-501 chromatography beads (Biorad, Richmond, Calif.) for 16 h at 4° C. The beads were cleared of unbound peptide by six cycles of gentle centrifugation followed by resuspension in $dH_2O$. The washed beads were then combined with 1 ml of antisera and mixed for 6 h at 4° C. Following centrifugation the supernatant was removed and the purified antibody stored as aliquots at −20° C.

Figure 10A:
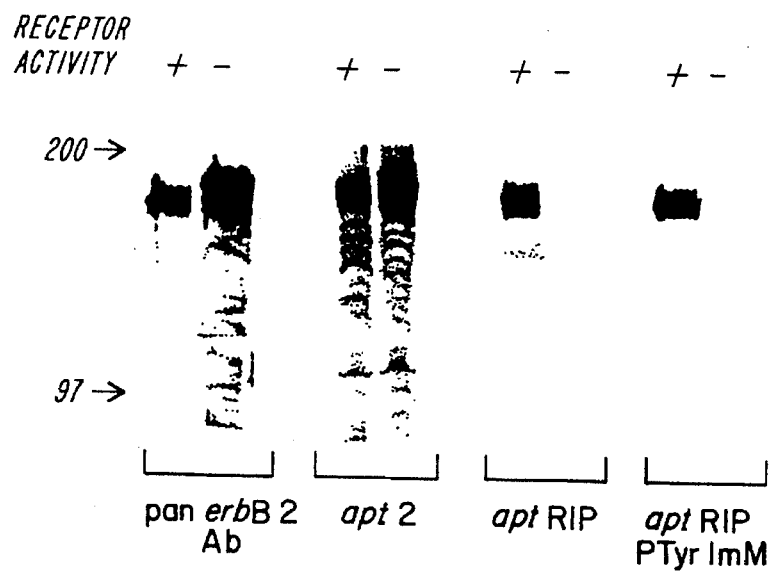
FIG. 10a shows reverse immunoaffinity purification (RIP) of antiphosphopeptide (apt) antiserum using an unphosphorylated peptide of identical sequence to the immunogen to adsorb non-activation-state-specific antibodies.

Unlike polyclonal antibodies to the unphosphorylated 1243–1255 peptide (Pab-1), crude apt antisera may preferentially recognize the activated p175 c-erbB-2 isoform. This visual distinction was attenuated by further boosts which increased immunoreactivity of both anti-p175 and anti-p185, but these higher-titer antisera were easily purified by the single-step reverse immunoaffinity procedure. Referring to FIG. 10a, high-titer antiphosphopeptide antiserum from one rabbit (apt-2) did not distinguish p175 and p185 prior to purification—similarly to commercially available (pan-erbB-2) antibodies. However, single-step reverse immunoaffinity purification (RIP) of the crude apt antiserum using the unphosphorylated peptide linked to agarose beads leads to near-monospecificity of p175 immunodetection. This is not antagonized by preincubation of the purified apt-2 antiserum (apt-RIP) with phosphotyrosine (PTyr 1mM), indicating that p175 immunodetection was not primarily due to non-receptor-specific antiphosphotyrosine antibodies.

Figure 10B:
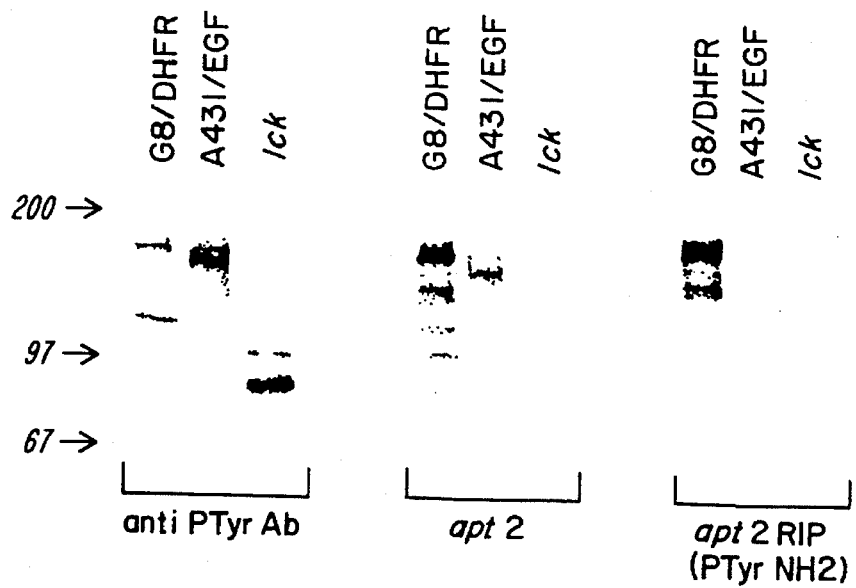
FIG. 10b shows reverse immunoaffinity purification (RIP) of apt antiserum using phosphotyramine (PTyr-NH$_2$) to adsorb non-protein-specific antiphosphotyrosine antibodies.

Although a minor degree of non-specific antiphosphotyrosine activity was detectable in two of the three rabbit antisera produced, this unwanted contamination was again readily removed by a reverse immunoaffinity purification strategy. Referring to FIG. 10b, apt-2 antiserum was noted to detect a small proportion of EGF receptor-associated phosphotyrosine as well as that seen in recombinant lck tyrosine kinase. However, adsorption of this antiserum to phosphotyramine (PTyr-$NH_2$) led to the disappearance of this immunoreactivity.

Activation-specific detection of the denatured and native forms of the c-erbB-2 receptor We have previously shown that the c-erbB-2 receptor in G8/DHFR cells is negatively transmodulated by exposure to calf serum, PDGF, the protein kinase C agonist tetradeconyl phorbol ester acetate (TPA) (Epstein et al., J. Biol. Chem., 265:10746–10751 (1990)), or increased extracellular calcium (Epstein et al., Cell Growth Differentiation 3:157–164 (1992)). Unlike total c-erbB-2 expression, p175 expression—as measured by apt immunoreactivity—is rapidly abrogated by such stimuli. Recognition of the native c-erbB-2 receptor appears equally activation-specific in immunoprecipitation experiments and is correspondingly useful in cell staining. Major differences in apt-1 immunoreactivity have also been demonstrated in human breast cancer and ovarian cancer cells.

The ability to distinguish activated vs. inactivated c-erbB-2 protein overexpression via the use of APHID could help distinguish subsets of tumors which differ in metastatic potential or therapeutic responsiveness. This would be of particular value in stage I (node-negative) disease where c-erbB-2 detection is currently of least clinical value.

Experimental procedures

Cells, cell lysis, and control antibodies

Stock cultures of G8/DHFR murine fibroblasts containing an amplified dicistronic rat c-neu/dihydrofolate reductase construct (a gift of Dr. Robert Weinberg, Whitehead Institute, Cambridge, Mass.) were maintained in Dulbecco's minimal essential medium (DME) supplemented with 10% bovine calf serum, glutamine, antibiotics and 0.3 μM methotrexate. All other cell lines were obtained from the American Type Culture Collection. Cell manipulation, immunoblotting protocols, polyacrylamide gel electrophoresis, and reagents were as previously described (Epstein et al., J. Biol. Chem., 265:10746–10751 (1990)). Phosphotyrosine was obtained from Sigma Chemical Co. (St. Louis, Mo.). Cells were lysed in 10 mM $Na_2HPO_4 \cdot 7H_2O$, 10 mM $NaH_2PO_4 \cdot H_2O$, 150 mM NaCl, 1% Nonidet P-40 (v/v), 10% glycerol (v/v), 50 mM sodium fluoride, 10 mM sodium pyrophosphate, plus protease inhibitors (sodium orthovanadate 1 mM, leupeptin 40 μM, aprotinin 10 μg/ml, phenylmethylsulfonylfluoride (PMSF) 1 mM, benzamidine HCl 50 μg/ml, and sodium molybdate 50 μg/ml). To provide negative phosphotyrosine controls, some G8/DHFR cell samples were treated with 10% bovine calf serum for 15 mins to transmodulate the c-erbB-2 receptor (Epstein et al., J. Biol.

Chem., 265:10746–10751 (1990)) and were then lysed in the absence of the tyrosine phosphatase inhibitor sodium orthovanadate. For immunoblotting, pAb-1 rabbit polyclonal antibody raised against the carboxyterminal 1243–1255 peptide sequence of the neu gene product (Triton Biosciences, Alameda, Calif.) was reconstituted in water and diluted 1:100 in TBST buffer (10 mM Tris-HCl, pH 8.0, 150 mM NaCl, 0.05% Tween-20), while monoclonal antiphosphotyrosine antibody (anti-PTyr) was purified over a S. aureus protein-A affinity column and used at a 1:1000 concentration. Cell samples were lysed following exposure to PDGF (30 ng/ml), EGF (100 ng/ml), TPA (100 µg/ml) or calcium chloride (10 mM). Control immunoprecipitation of the c-erbB-2 receptor was performed using commercially available antibodies (Oncogene Science, Manhasset, N.Y.; Triton Biosciences, Alameda, Calif.).

Competition for antiphosphotyrosine antibody binding

B104-1-1 cells expressing the constitutively activated c-erbB-2 receptor were lysed and immunoprecipitated with 1:100 antiphosphotyrosine antibody prior to immunoblotting with the same antibody at 1:1000. The antibody was preincubated for 30 mins with either KLH, 1 mM phosphotyrosine (PTyr), synthetic phosphopeptide (PTyr peptide), unphosphorylated peptide (Thr peptide), KLH-phosphopeptide conjugate (PTyr conjugate) or KLH-unphosphorylated peptide conjugate (Thr conjugate).

Determination of immunoreactivity of rabbit antisera following phosphopeptide immunization The polyclonal Pab-1 antibody (raised against unphosphorylated 1243–1255 c-erbB-2 peptide) was used at 1:100, while antiphosphotyrosine (anti-PTyr), apt, and preimmune antibodies were used at 1:1000. EGF receptor-expressing A431 cells were exposed for 15 mins to EGF 100 ng/ml prior to lysis, and were then electrophoresed alongside G8/DHFR cell lysates containing activated or inactivated c-erbB-2 receptors. Immunoblots were incubated with unpurified apt antisera (1:1000), apt antisera preincubated with 1 mM phosphotyrosine for 30 mins, or antiphosphotyrosine antibody (1:1000).

EXAMPLE II

Figure 11:
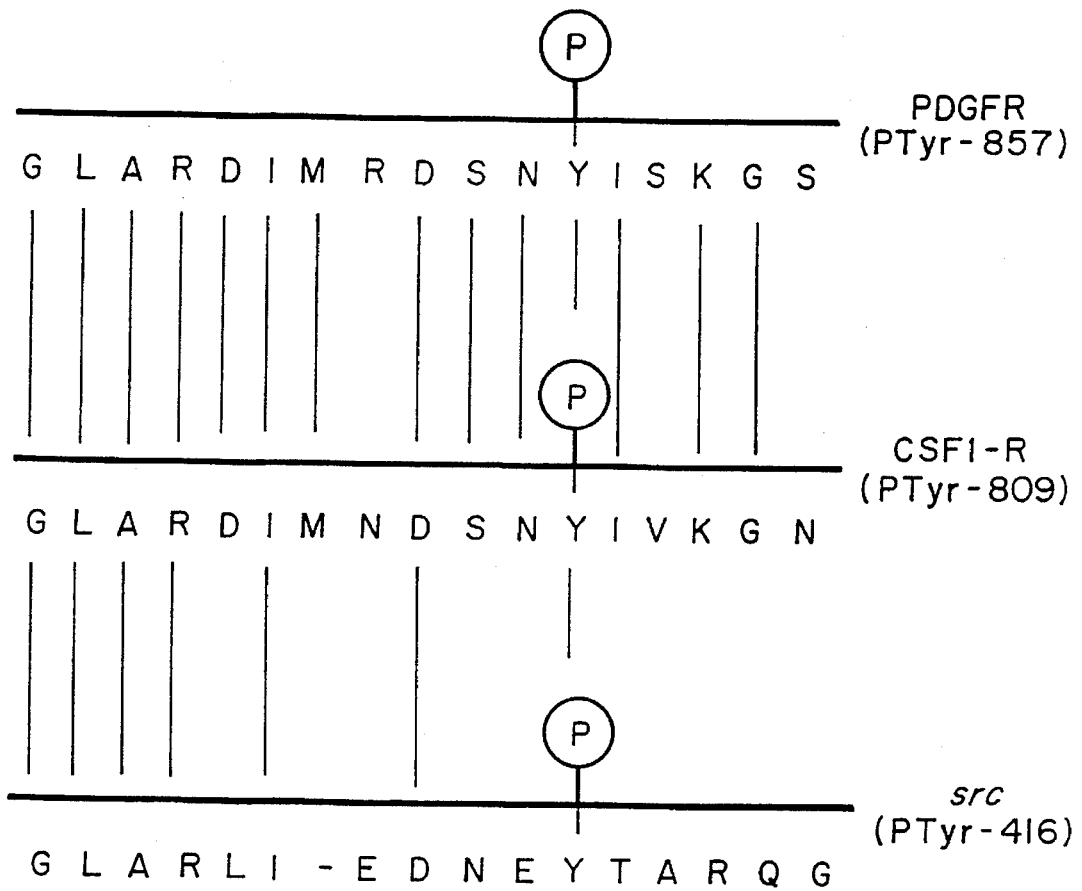
FIG. 11 shows the amino acid sequence homology between the PDGF and CSF-1 receptor (SEQ ID NO:10) tyrosine kinases and the src non-receptor (SEQ ID NO:11) tyrosine kinase.

The receptor for platelet-derived growth factor (PDGF) is a major signaling molecule in human connective tissues and in the developing brain (Williams, Science 248:1564–1570 (1989)). Like c-erbB-2 and the EGF receptor, the PDGF receptor is a member of the tyrosine kinase superfamily, but has evolved as part of a structurally distinct subfamily including the colony-stimulating factor-1 (CSF-1) receptor and the kit gene product; a third major receptor tyrosine kinase subfamily is represented by the insulin receptor (IR) and the closely-related receptor for insulin-like growth factor-1, or IGF-1 (FIG. 7). A major autophosphorylation site of the human PDGF receptor is found at tyrosine 857 within the kinase insert domain (Kazlauskas & Cooper, Cell 58:1121–1133 (1989)). This autophosphorylation sequence bears strong homology to a sequence similarly positioned in the kinase insert of the CSF-1 receptor (FIG. 11).

We expect that activation-specific antibodies to the phosphorylated tyrosine 857 peptide sequence of the PDGF receptor—and hence to the activated receptor itself—will be readily obtainable using the APHID technique. In addition to the potential value of such antibodies in basic research studies of cell growth regulation and embryogenetic interactions, activation-specific PDGF receptor detection should prove useful in immunophenotyping human brain tumors (Hermansson et al., Proc. Natl. Acad. Sci., USA, 85:7748–7752 (1988)), sarcomas (Fahrer et al., Int. J. Cancer, 44:652–657 (1989)), and thyroid carcinomas (Heldin et al., Proc. Natl. Acad. Sci., USA, 85:9302–9306 (1988)).

Similarly, apt antibodies to CSF-1 receptors could be used to detect autocrine, paracrine or mutation-associated activation of these receptors in hematologic and other malignancies. Such antibodies could also be used in the investigation of unexplained leucocytosis, and in the assessment of likely therapeutic benefit in patients receiving CSF therapy for clinical problems such as aplastic anemia, cancer chemotherapeutic cell support, and bone marrow transplantation.

EXAMPLE III

It is notable that both of the sequences discussed above retain major homology to a key autophosphorylation site of the src proto-oncogene product (FIG. 11), a non-receptor tyrosine kinase which acts as a critical intracellular signaling protein.

The src family encompasses numerous members including the fyn and lck molecules which regulate immune cell function. By virtue of their homologous structure and tyrosine-phosphorylation-dependent activation (Hanks et al., Science, 241:42–52 (1988)), we expect that activation-specific antibodies to src-like proteins would be readily obtainable using APHID technology. Like other proto-oncogene products, src plays a central role in normal intracellular signaling, while also being implicated in the pathogenesis of some human malignancies. For example, Cartwright et al. showed a two-fold increase in c-src expression and ten-fold increase in c-src tyrosine kinase activity in colonic adenomas and carcinomas compared to adjacent normal mucosa (Proc. Natl. Acad. Sci., USA, 87:558–562 (1990)). This molecule presents a particularly attractive option for applying the APHID approach, since tyrosine-416 represents an activation-specific autophosphorylation sequence (Yarden et al., Nature 323:226–232 (1986)) while phosphorylation of Tyr-527 is associated with negative regulation (Cobb et al., Mol. Cell. Biol., 11:5832–5838 (1991)). Hence, application of any or all of the approaches outlined in FIGS. 3–6 would be expected to yield antibodies distinguishing both the activated and inactivated src molecule isoforms. This could be useful in further studying the intracellular signaling changes which occur in early human tumors and during tumor progression, with possible clinical and therapeutic implications arising from such studies. Many other key intracellular signaling proteins—such as phospholipase C (Kim et al., Cell, 65:435–441 (1991)) and the serine/threonine kinase ERK family (which are phosphorylated on tyrosine; Boulton et al., Cell, 65:663–675 (1991))—should prove similarly amenable to APHID-style immunophenotypic characterization.

EXAMPLE IV

Immunodetection of the Ser-315-phosphorylated P53 gene product

Many proteins alter their metabolic activity by phosphorylation of serine or threonine residues. Kinases responsible for such phosphorylation include protein kinase C, protein kinase A, and the casein kinases. Another kinase, the cell-cycle regulator cdc2, phosphorylates two key nuclear factors, the retinoblastoma protein, Rb (Lees et al., EMBO J., 10:4279–4290 (1991)), and the p53 gene product (Bischoff et al., Proc. Natl. Acad. Sci. USA, 87:4766–4770 (1990)). Both of these nuclear factors have been implicated as tumor suppressors which control cell-cycle progression. Wild-type unphosphorylated p53 is associated with cell quiescence, but cell proliferation is associated with phosphorylation of p53 on serine-315, indicating that p53 phosphorylation may abrogate the antiproliferative activity of this molecule (Bischoff et al., op. cit.). Allelic loss of the p53 gene is recognized in many common human tumors, and mutations within this gene have been implicated in some familial breast cancer syndromes (Malkin et al., Science, 250:1233–1238 (1990)).

Mutant forms of the protein may be recognized by a commercially available monoclonal antibody (Gannon et al., EMBO J., 9:1595–1602 (1990)). No evidence of mutated p53 has been reported in early breast neoplasia, however, and overall expression of p53 does not correlate with the presence of mutations in human breast tumors (Thompson et al., Int. J. Cancer, 50:528–532 (1992)). These findings raise the possibility that immunodetection of Ser-315-phosphorylated p53 may provide a clinically useful marker for identifying neoplastic and preneoplastic cells which are undergoing dysregulated proliferation, either as a result of primary DNA mutations or as a secondary effect of other tumorigenic stimuli. Such a marker could aid in the clinical characterization of early breast tumors discovered at screening mammography, and could help dictate the need for adjuvant systemic or local (e.g., mastectomy or irradiation) therapy in such patients.

EXAMPLE V

Immunodetection of the Ser-675-phosphorylated progesterone receptor

Current detection of primary breast tumor hormone (estrogen and progesterone) receptors predicts a 60–70% likelihood of responsiveness to hormonal therapy in the event of subsequent tumor dissemination. The false-positive predictivity of this measure has long been a matter for debate. One possibility is that conventional antibody-based or radioimmunoassay techniques may detect functionally defective receptors. Application of APHID methodology may be able to selectively identify tumors expressing hormone receptors which are actively functioning and (thus) contributing to disease growth and progression. Treatment of such tumors would be expected to yield a far higher response rate than that currently obtainable, thus permitting patients with APHID-negative hormone receptors to commence more beneficial therapies. Recent studies have shown that a 20-fold increase in phosphorylation of the Ser-530 residue of the chicken progesterone receptor accompanies receptor activation, and that this is probably due to the activity of a proline-dependent kinase (Denner et al., J. Biol. Chem. 265:16548–16555 (1990)). The Ser-530 moiety corresponds to the homologous Ser-675 of the human progesterone receptor (Misrahi et al., Biochem. Biophys. Res. Comm. 143:740–748 (1987); Denner et al., J. Biol. Chem. 265:16548–16555 (1990)). Hence, immunodetection at this phosphopeptide site may be clinically helpful in identifying tumors expressing functional ligand-activated receptor, and thus in more accurately predicting the utility of endocrine manipulations in both adjuvant and metastatic breast cancer management.

EXAMPLE VI

Identification of PDGF receptor agonists or antagonists using apt antibodies in "high flux" drug screening protocols Apt antibodies raised against growth factor receptors, tyrosine kinases, and other regulatory phosphoproteins can be used in "high flux" or entry level drug screening protocols to identify pharmaceutically useful compounds which act as growth factor agonists or antagonists. Generally, two broad approaches to high flux drug screens are proposed. Cell-based approaches use an indicator cell line that is exposed to the compound to be tested. This approach is thought to quickly eliminate drugs that have solubility or membrane permeability problems. Protein- or enzyme-based screens, on the other hand, use purified proteins and can identify drugs that react with the receptor directly. These compounds may then be chemically modified to allow them to cross cell membranes.

In the cell-based assay, an indicator cell line that expresses platelet derived growth factor (PDGF) receptors can be cultured in 96-well microtiter vessels directly on top of sterile nitrocellulose filters. A fixed dose of PDGF ligand is added to each well together with a compound to be tested for antagonist activity. After five minutes the cells are lysed with detergent directly upon the surface of the nitrocellulose filter. Each of the 96 culture lysates are then processed by conventional "Western Blot" protocols well known in the art (e.g., as described in Towbin et al., Proc. Natl. Acad. Sci. USA 76:4350–4354 (1979)) using apt antibodies specific for the activated form of PDGF receptor. Cultures which failed to react with the antibody would indicate a potential PDGF antagonist activity. This procedure could readily be modified to screen for drugs with PDGF agonist activity by culturing indicator cells as described above, exposing them to compounds to be tested but not to PDGF ligand, and challenging the cells with antibodies specific for the activated form of PDGF receptor. Cell lysates which react with the antibody would suggest that the tested compound is a potential PDGF agonist.

In the protein-based assay, biologically active recombinant PDGF receptor protein is produced using a baculovirus vector/insect host cell system which is well known in the art (e.g., as described in Morrison et al., Cell 58:649–657 (1989)). Receptor produced in this way is constitutively autophosphorylated and kinase-active in solution. However, phosphatase treatment will dephosphorylate the recombinant receptor and yield milligram quantities of receptor for an entry level protein-based drug screen. After addition of sodium orthovanadate to deactivate the phosphatase, aliquots of the dephosphorylated recombinant PDGF receptor are dispensed into 96 microtiter wells together with PDGF ligand, ATP, and compounds to be tested for antagonist activity. After several minutes, the reaction mixtures are dispensed onto nitrocellulose filters. Each of the 96 reaction mixtures are then processed by conventional "Western Blot" protocols using antibodies specific for the activated form of PDGF receptor. Reaction mixtures which failed to react with the antibody would indicate a potential PDGF antagonist. To screen for drugs with PDGF agonist activity, recombinant receptor (prepared as described above) is exposed to compounds to be tested and ATP, and the reaction mixture is challenged with antibodies specific for the activated form of PDGF receptor. Reaction mixtures which react with the antibody would suggest that the compound tested is a potential PDGF agonist.

The above examples have given many clinically important uses for apt antibodies in diagnostic and screening protocols. Suggestions have also been made with respect to the therapeutic implications of diagnostic information. Apt antibodies could be provided in a kit to be used in a diagnostic laboratory setting in characterizing the activation state of the reversibly phosphorylated protein of interest. The kit would contain the components required for the extraction of a specific tissue sample and the components necessary for use in a binding assay, including the appropriate apt antibody.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A method for producing antibody that specifically binds to one of the two isoforms of a reversibly phosphorylated protein and does not bind to the other isoform of said protein nor to proteins other than said protein, said method comprising the steps of:

a) providing a peptide consisting essentially of a reversible phosphorylation site of said protein, a phosphorylatable amino acid in said reversible phosphorylation site being in the phosphorylation state of one of the two isoforms of said protein, said phosphorylation state having been achieved chemically and not enzymatically;

b) raising antibodies against said peptide;

c) isolating a population of antibodies reactive with said peptide;

d) screening said population for antibodies not reactive with said peptide wherein said peptide is in the phosphorylation state of the other isoform of said protein, said phosphorylation state having been achieved chemically and not enzymatically;

e) collecting antibodies identified in screening step (d); and f) testing antibodies collected in step (e) to verify that the antibodies specifically bind said protein and not proteins other than said protein.

2. The method of claim 1 wherein said two isoforms represent functionally divergent forms of said protein.

3. The method of claim 1 wherein said two isoforms represent active and inactive forms of said protein.

4. The method of claim 3 wherein said protein is active in the phosphorylated state.

5. The method of claim 3 wherein the protein is inactive in the phosphorylated state.

6. The method of claim 1 wherein the protein is phosphorylated on a tyrosine residue.

7. The method of claim 1 wherein the protein is phosphorylated on a serine and/or threonine residue.

8. The method of claim 1 wherein the protein is a tyrosine kinase.

9. The method of claim 1 wherein the protein is a serine or threonine kinase.

10. The method of claim 1 wherein the protein is a receptor.

11. The method of claim 10 wherein said receptor is a hormone receptor.

12. The method of claim 10 wherein said receptor is a growth factor receptor.

13. The method of claim 10 wherein said receptor is the c-erbB-2 receptor.

14. Antibody that specifically binds to a reversible tyrosine phosphorylation site of a reversibly phosphorylated protein in its phosphorylated isoform and does not bind to the non-phosphorylated isoform of said protein, nor to proteins other than said protein.

15. Antibody that specifically binds to a reversible tyrosine phosphorylation site of a reversibly phosphorylated protein in its non-phosphorylated isoform and does not bind to the phosphorylated isoform of said protein, nor to proteins other than said protein.

16. Antibody that specifically binds to a reversible phosphorylation site of the c-erbB-2 receptor in its active form and does not bind to the inactive form of said c-erbB-2 receptor, nor to proteins other than said c-erbB-2 receptor.

17. A method for screening for metastatic potential of tumors in patients with node-negative breast cancer comprising reacting the antibody of claim 16 with tumor tissue from said patient;

detecting the extent of binding of said antibody to said tissue; and correlating the extent of binding of said antibody with metastatic potential.

18. A kit for use in identifying the activation state of a reversibly phosphorylated protein in a sample by determining whether said protein is in its active or inactive isoform, said kit comprising components required for extraction of said sample; and components necessary for use in a binding assay, said binding assay components comprising antibody that specifically binds to a reversible phosphorylation site of the active isoform of said protein and does not bind to the inactive isoform of said protein nor to proteins other than said protein.

19. A kit for use in identifying the activation state of a reversibly phosphorylated protein in a sample by determining whether said protein is in its active or inactive isoform, said kit comprising components required for extraction of said sample; and components necessary for use in a binding assay, said binding assay components comprising antibody that specifically binds to a reversible phosphorylation site of the inactive isoform of said protein and does not bind to the active isoform of said protein nor to proteins other than said protein.

20. The kit of claim 18 or claim 19 wherein said antibody is a monoclonal antibody.

21. The kit of claim 18 or 19 wherein said components necessary for use in a binding assay further comprise a second indicator antibody linked to an indicator reagent.

22. The kit of claim 21 wherein said indicator reagent is selected from a group consisting of fluorescent, colorimetric, immunoperoxidase and isotopic reagents.

* * * * *

UNITED STATES PATENT AND TRADEMARK OFFICE
CERTIFICATE OF CORRECTION

PATENT NO.  :  5,599,681
DATED       :  February 4, 1997
INVENTOR(S) :  Richard J. Epstein et al.

It is certified that error appears in the above-indentified patent and that said Letters Patent is hereby corrected as shown below:

Column 2, line 14, "Kinasein.-active" should read --kinase-inactive--.

Column 4, line 11, "8a SEQ" should read --8a; SEQ--.

Column 4, line 12, "8b SEQ" should read --8b; SEQ--.

Column 4, line 28, "PDGF and" should read --PDGF (SEQ ID NO:9)--.

Column 4, line 44, "1243-1255" should read --1243-1255 (SEQ ID NO:1)--.

Column 22, line 22, "components required for extraction of said sample; and" should be deleted.

Column 22, line 25, "reversible phosphorylation" should read --reversible tyrosine phosphorylation--.

Column 22, line 34, "components required for extraction of said sample; and" should be deleted.

Column 22, line 37, "reversible phosphorylation" should read --reversible tyrosine phosphorylation--.

UNITED STATES PATENT AND TRADEMARK OFFICE
CERTIFICATE OF CORRECTION

PATENT NO. : 5,599,681
DATED : February 4, 1997
INVENTOR(S) : Richard J. Epstein et al.

It is certified that error appears in the above-indentified patent and that said Letters Patent is hereby corrected as shown below:

Column 22, line 49, add claim 23 as follows --The kit of claim 18 or claim 19 wherein said binding assay components further comprise antibody that specifically binds to the active and inactive isoforms of said protein and does not bind to proteins other than said protein.--

Signed and Sealed this

Sixteenth Day of September, 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,599,681
DATED : February 4, 1997
INVENTOR(S) : Epstein et al.

Page 1 of 1

It is certified that error appears in the above-identified patent and that said Letters Patent is hereby corrected as shown below:

<u>Title page,</u>
Item [75], Inventors, should read -- Richard J. Epstein, Brookline MA, Charles D Stiles, Newton MA, and Brian J. Druker, Portland OR --.

Signed and Sealed this

Thirteenth Day of June, 2006

JON W. DUDAS
*Director of the United States Patent and Trademark Office*

(12) REEXAMINATION CERTIFICATE (4391st)
United States Patent
Epstein et al.

(10) Number: US 5,599,681 C1
(45) Certificate Issued: Jul. 3, 2001

(54) ACTIVATION-STATE-SPECIFIC PHOSPHOPROTEIN IMMUNODETECTION

(75) Inventors: Richard J. Epstein, Brookline; Charles D. Stiles, Newton, both of MA (US)

(73) Assignee: Dana-Farber Cancer Institute, Inc., Boston, MA (US)

Reexamination Request:
No. 90/005,087, Aug. 26, 1998

Reexamination Certificate for:
Patent No.: 5,599,681
Issued: Feb. 4, 1997
Appl. No.: 08/324,421
Filed: Oct. 13, 1994

Certificate of Correction issued Sep. 16, 1997.

Related U.S. Application Data

(63) Continuation of application No. 07/918,370, filed on Jul. 23, 1992, now abandoned, which is a continuation-in-part of application No. 07/866,728, filed on Apr. 10, 1992, now abandoned.

(51) Int. Cl.[7] .................................................. G01N 33/574
(52) U.S. Cl. .................... 435/7.23; 435/7.4; 436/543; 436/547; 436/548; 530/387.7; 530/387.9; 530/388.8; 530/388.85; 530/389.7

(58) Field of Search ..................................... 435/7.23, 7.4; 436/547, 543, 548; 530/387.7, 387.9, 388.8, 388.85, 389.7

(56) References Cited

PUBLICATIONS

Lee, Virginia.–Y. et al., A Major Subunit of Paired Helical Filaments and Derivatized Forms of Normal Tau, Science, (Feb., 1991), pp. 675–678.

*Primary Examiner*—Sheila J Huff

(57) ABSTRACT

Activation-state-specific and protein-specific antiphosphoprotein antibodies and methods for their production are disclosed. Also disclosed are methods for evaluating the prognosis and therapeutic outcome for patients using the antiphosphoprotein antibodies and methods for characterizing the activation state of a reversibly phosphorylated protein, kits including the antibodies for use in characterizing the activation state of a protein, and methods for evaluating the agonist or antagonist activity of pharmaceutically useful compounds towards the conversion of a specific protein from its inactive to its active state.

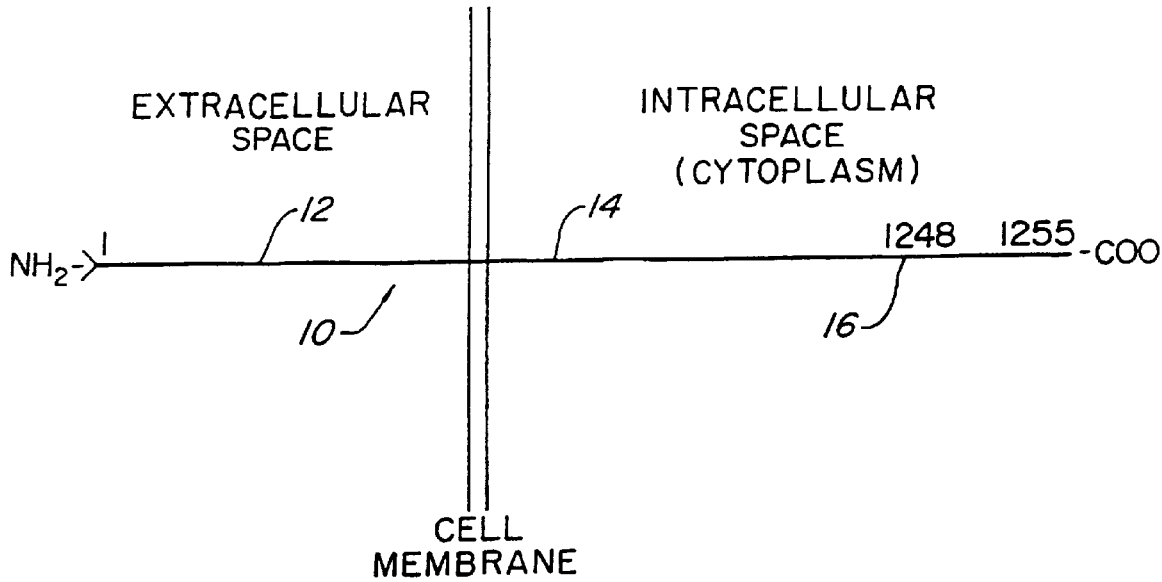

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 14–22 is confirmed.

Claim 1 is determined to be patentable as amended.

Claim 2–13, dependent on an amended claim, are determined to be patentable.

New claims 23–33 are added and determined to be patentable.

1. A method for producing *a desired* antibody that specifically binds to one of the two isoforms of a reversibly phosphorylated protein and does not bind to the other isoform of said protein nor to proteins other than said protein, said method comprising the steps of:
   a) providing a peptide consisting essentially of a reversible phosphorylation site of said protein, a phosphorylatable amino acid in said reversible phosphorylation site being in the phosphorylation state of one of the two isoforms of said protein, said phosphorylation state having been achieved chemically and not enzymatically;
   b) raising antibodies against said peptide;
   c) isolating a population of antibodies reactive with said peptide;
   d) [screening] *purifying from* said population [for] antibodies not reactive with said peptide *having said phosphorylatable amino acid in the same phosphorylation state as in step (a), wheren said purifying is carried out by contacting said population with said* peptide *that* is in the phosphorylation state of the other isoform of said protein, said phosphorylation state having been achieved chemically and not enzymatically, *to remove antibodies from said population that bind to said peptide in said other isoform*;
   e) collecting *non-reactive* antibodies identified in [screening] *purification* step (d); and
   f) testing antibodies collected in step (e) to verify that the antibodies specifically bind *to one of the two isoforms of* said *reversibly phosphorylated* protein and not *to the other isoform of said protein or to* proteins other than said protein.

23. *The method of claim 1, further comprising the step of (g) contacting said population of antibodies with the reversibly phosphorylated amino acid of said phosphorylation site, wherein said amino acid can be phosphorylated or non-phosphorylated.*

24. *The method of claim 1, further comprising the step of (g) contacting said population of antibodies with said peptide that is of the same isoform as the protein for which the desired antibody is specific.*

25. *A method for producing a desired antibody that specifically binds to one of the two isoforms of a reversibly phosphorylated protein and does not bind to the other isoform of said protein nor to proteins other than said protein, said method comprising the steps of;*
   *a) providing a peptide consisting essentially of a reversible phosphorylation site of said protein, a phosphorylatable amino acid in said reversible phosphorylation site being in the phosphorylation state of one of the two isoforms of said protein, said phosphorylation state having been achieved chemically and not enzymatically;*
   *b) raising antibodies against said peptide;*
   *c) isolating a population of antibodies reactive with said peptide;*
   *d) screening said antibodies against a first peptide that is in the phosphorylation state of one isoform of the protein and against a second peptide that is in the phosphorylation state of the other isoform of the protein; and*
   *e) isolating the desired antibody resulting from conducting screening step (d).*

26. *The method of claim 1, wherein said testing step (f) comprises reacting said antibodies tested in step (f) with a whole-cell lysate.*

27. *The method of claim 25, further comprising the step of (f) reacting said antibody isolated in step (e) with a whole-cell lysate to determine that it is not reactive with other proteins.*

28. *A method for producing antibody that specifically binds to one of the two isoforms of a reversibly phosphorylated tyrosine kinase and does not bind to the other isoform of said tyrosine kinase nor to proteins other than said tyrosine kinase, said method comprising the steps of:*
   *a) providing a peptide consisting essentially of a reversible phosphorylation site of said tyrosine kinase, a phosphorylatable amino acid in said reversible phosphorylation site being in the phosphorylation state of one of the two isoforms of said tyrosine kinase, said phosphorylation state having been achieved chemically and not enzymatically;*
   *b) raising antibodies against said peptide;*
   *c) isolating a population of antibodies reactive with said peptide;*
   *d) screening said population for antibodies not reactive with said peptide wherein said peptide is in said phosphorylation state of the other isoform of said tyrosine kinase, said phosphorylation state having been achieved chemically and not enzymatically;*
   *e) collecting antibodies identified in screening step (d); and*
   *f) testing antibodies collected in step (e) to verify that the antibodies specifically bind to said tyrosine kinase and not to proteins other than said tyrosine kinase.*

29. *A method for producing antibody that specifically binds to one of the two isoforms of a reversibly phosphorylated serine or theronine kinase and does not bind to the other isoform of said serine or threonine kinase nor to proteins other than said serine or threonine kinase, said method comprising the steps of:*
   *a) providing a peptide consisting essentially of a reversible phosphorylation site of said serine or threonine kinase, a phosphorylatable amino acid in said reversible phosphorylation site being in the phosphorylation state of one of the two isoforms of said serine or threonine kinase, said phosphorylation state having been achieved chemically and not enzymatically;* b) raising antibodies against said peptide;

c) isolating a population of antibodies reactive with said peptide;

d) screening said population for antibodies not reactive with said peptide wherein said peptide is in said phosphorylation state of the other isoform of said serine or threonine kinase, said phosphorylation state having been achieved chemically and not enzymatically;

e) collecting antibodies identified in screening step (d); and f) testing antibodies collected in step (e) to verify that the antibodies specifically bind to said serine or threonine kinase and not to proteins other than said serine or threonine kinase.

30. A method for producng antibody that specifically binds to one of the two isoforms of a reversibly phosphorylated receptor and does not bind to the other isoform of said receptor nor to proteins other than said receptor, said method comprising the steps of:

a) providing a peptide consisting essentially of a reversible phosphorylation site of said receptor, a phosphorylatable amino acid in said reversible phosphorylation site being in the phosphorylation state of one of the two isoforms of said receptor, said phosphorylation state having been achieved chemically and not enzymatically;

b) raising antibodies against said peptide;

c) isolating a population of antibodies reactive with said peptide;

d) screening said population for antibodies not reactive with said peptide wherein said peptide is in said phosphorylation state of the other isoform of said receptor, said phosphorylation state having been achieved chemically and not enzymatically;

e) collecting antibodies identified in screening step (d); and f) testing antibodies collected in step (e) to verify that the antibodies specifically bind to said receptor and not to proteins other than said receptor.

31. The method of claim 30 wherein said receptor is a hormone receptor.

32. The method of claim 30 wherein said receptor is a growth factor receptor.

33. The method of claim 30 wherein said receptor is the c-erbB-2 receptor.

\* \* \* \* \*